United States Patent
Lei et al.

(10) Patent No.: US 12,252,473 B2
(45) Date of Patent: Mar. 18, 2025

(54) PREPARATION METHODS OF QUINOLONE COMPOUNDS AND INTERMEDIATES THEREOF

(71) Applicant: Chongqing University of Arts and Sciences, Chongqing (CN)

(72) Inventors: Jie Lei, Chongqing (CN); Zhongzhu Chen, Chongqing (CN); Zhigang Xu, Chongqing (CN); Dianyong Tang, Chongqing (CN); Jiayu Xu, Chongqing (CN); Haoyi Zhou, Chongqing (CN); Dandan Xia, Chongqing (CN); Yao Liu, Chongqing (CN); Yihua Cao, Chongqing (CN); Jie Luo, Chongqing (CN)

(73) Assignee: Chongqing University of Arts and Sciences, Chongqing (CN)

( * ) Notice: Subject to any disclaimer, the term of this patent is extended or adjusted under 35 U.S.C. 154(b) by 0 days.

(21) Appl. No.: 18/261,960

(22) PCT Filed: May 5, 2022

(86) PCT No.: PCT/CN2022/090989
§ 371 (c)(1),
(2) Date: Jul. 18, 2023

(87) PCT Pub. No.: WO2023/201780
PCT Pub. Date: Oct. 26, 2023

(65) Prior Publication Data
US 2024/0400522 A1    Dec. 5, 2024

(30) Foreign Application Priority Data
Apr. 18, 2022 (CN) .......................... 202210437152.2

(51) Int. Cl.
*C07D 241/04* (2006.01)
*C07D 213/74* (2006.01)
*C07D 221/04* (2006.01)
*C07D 491/056* (2006.01)

(52) U.S. Cl.
CPC ......... *C07D 241/04* (2013.01); *C07D 213/74* (2013.01); *C07D 221/04* (2013.01); *C07D 491/056* (2013.01)

(58) Field of Classification Search
CPC .. C07D 241/04; C07D 213/74; C07D 221/04; C07D 491/056
USPC ....................................................... 564/336
See application file for complete search history.

(56) References Cited

FOREIGN PATENT DOCUMENTS

| CN | 102040591 A | 5/2011 |
| CN | 105130892 A | 12/2015 |

OTHER PUBLICATIONS

Iaroshenko et al., "Synthesis of 4-quinolones, benzopyran derivatives and other fused systems based on the domino ANRORC reactions of (ortho-fluoro)-3-benzoylchromones," *RSC Adv.* 5:28717-28724 (2015).
Zhang et al., "Efficient Synthesis of 7H-Chromeno[3,2-c]quinoline-5-ium Salts and Quinolin-4-ones through Acid-Promoted Cascade Reaction of 3-Formylchromones and Anilines," *ChemistrySelect* 7:e202104611, 6 pages (2022).

*Primary Examiner* — Ana Z Muresan
(74) *Attorney, Agent, or Firm* — Seed IP Law Group LLP

(57) ABSTRACT

The present application relates to processes for the preparation of quinolone compounds and intermediates thereof, particularly to processes for the preparation of quinolones and pharmaceutical intermediates of the quinolones. In particular, the present application provides a process for the preparation of a compound of Formula I, and a process for the synthesis of quinolone compounds using the compound of Formula I as an intermediate. The process for the preparation of the compound of Formula I comprises the steps of:
    reacting a compound of Formula A with $R^5NH_2$ and $R^6Cl$ in the presence of a base to form the compound of Formula I,

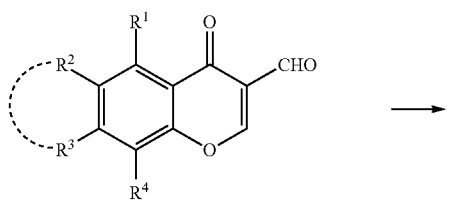

Formula A

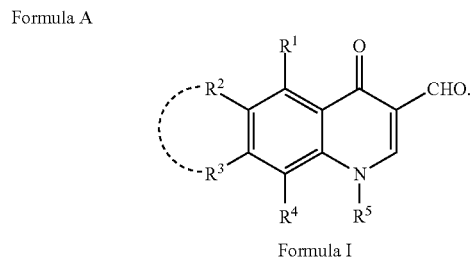

Formula I

12 Claims, No Drawings

PREPARATION METHODS OF QUINOLONE COMPOUNDS AND INTERMEDIATES THEREOF

CROSS-REFERENCE TO RELATED APPLICATION

The present application claims the priority to and the benefit of Chinese Patent Application No. 202210437152.2 filed with the China National Intellectual Property Administration on Apr. 18, 2022, which is incorporated herein by reference in its entirety.

TECHNICAL FIELD

The present application relates to the field of pharmaceutical chemistry. In particular, the present application relates to processes for the preparation of quinolone compounds and intermediates thereof, particularly quinolones and pharmaceutical intermediates of quinolones.

BACKGROUND

As drug backbones, quinolones are widely used in antibacterial and anticancer therapy, and the treatment of cystic fibrosis, etc, and have many advantages, such as broad antibacterial spectrum, high pharmaceutical activity, low toxicity, and high efficacy.

Currently, there are three main processes for the synthesis of quinolone drugs:
(a) Condensation of aniline derivatives with diethyl ethoxymethylene malonate: allowing ortho-functionalization of the amine group under the condition of polyethyl phosphate or polyphosphoric acid, and then undergoing cyclization to obtain a key intermediate; functionalizing the nitrogen atom of the quinoline by an alkylation reaction to obtain quinolinones containing a substituent; and finally undergoing hydrolysis, acidification, and other steps to obtain the quinolones. Process (a) requires the use of more expensive EMME reaction starting materials, and during the cyclization using PPA and $POCl_3$ in the second step, the selectivity of the reaction is not high enough, resulting in a low yield.
(b) Using ethyl benzoylacetate as a starting material, reacting ethyl benzoylacetate with triethyl orthoformate, and then subjecting the resultant compound to condensation with a fatty amine to form an enamine dicarbonyl compound; subjecting the enamine dicarbonyl compound to intramolecular nucleophilic substitution reaction under basic condition to obtain a cyclic intermediate, and then hydrolyzing the cyclic intermediate under HCl condition to obtain a quinolone intermediate. The starting material ethyl 2-fluorobenzoyl acetate in Process (b) is expensive, and the acetal reagent triethyl orthoformate is a pungent liquid, which has a low melting point and boiling point and is not easily stored.
(c) Using o-fluorobenzoic acid as a starting material, and after chloroformylation, coupling the acyl chloride with ethyl N,N-dimethylaminoacrylate to form enamine intermediates, and allowing amine substitution reaction between an amine and an enamine dicarbonyl compound; subjecting the resultant compound to intramolecular cyclization under a basic condition to obtain a precursor of quinolone, and then hydrolyzing the quinolone prodrug to obtain the target product. Although the starting material o-fluorobenzoic acid in process (c) is readily available, this process requires five steps to obtain the precursor of quinolone, and the operations are complicated.

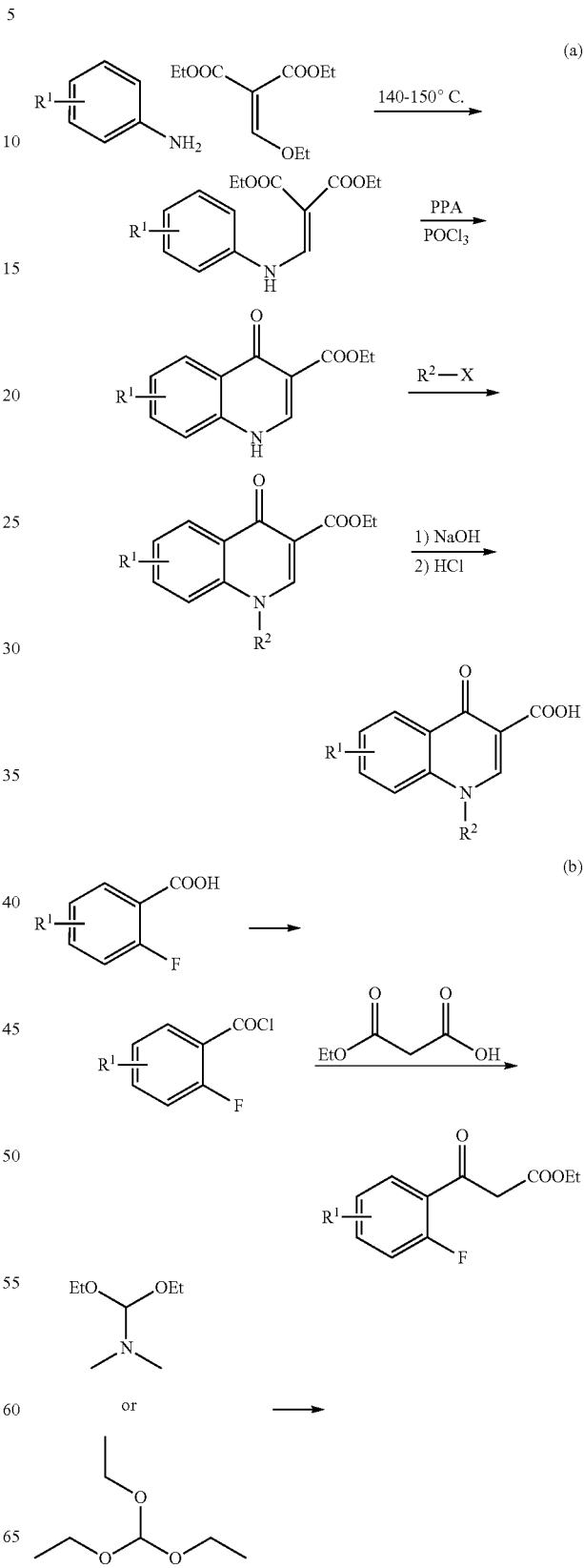

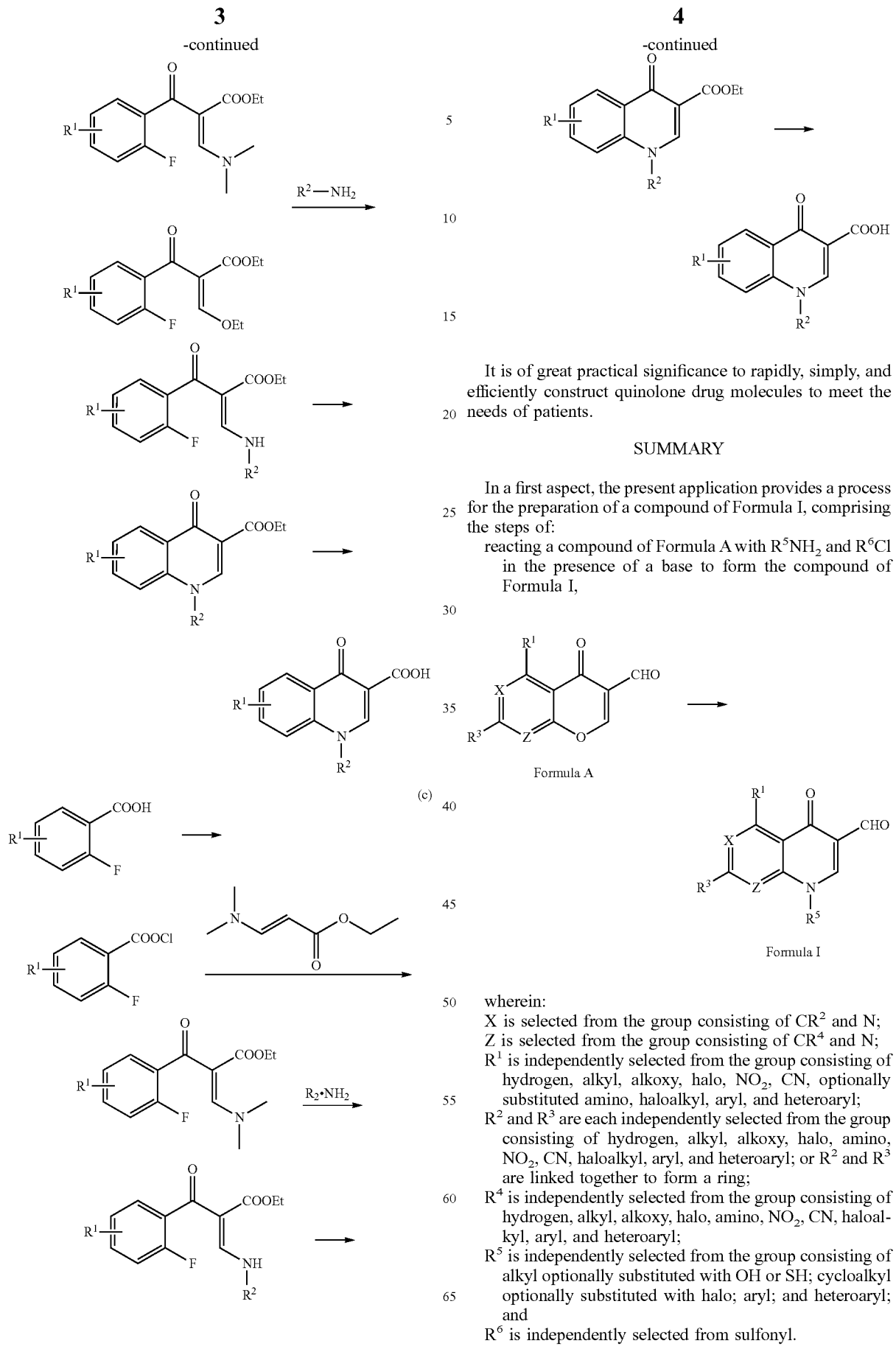

It is of great practical significance to rapidly, simply, and efficiently construct quinolone drug molecules to meet the needs of patients.

SUMMARY

In a first aspect, the present application provides a process for the preparation of a compound of Formula I, comprising the steps of:

reacting a compound of Formula A with $R^5NH_2$ and $R^6Cl$ in the presence of a base to form the compound of Formula I, wherein:
X is selected from the group consisting of $CR^2$ and N;
Z is selected from the group consisting of $CR^4$ and N;
$R^1$ is independently selected from the group consisting of hydrogen, alkyl, alkoxy, halo, $NO_2$, CN, optionally substituted amino, haloalkyl, aryl, and heteroaryl;
$R^2$ and $R^3$ are each independently selected from the group consisting of hydrogen, alkyl, alkoxy, halo, amino, $NO_2$, CN, haloalkyl, aryl, and heteroaryl; or $R^2$ and $R^3$ are linked together to form a ring;
$R^4$ is independently selected from the group consisting of hydrogen, alkyl, alkoxy, halo, amino, $NO_2$, CN, haloalkyl, aryl, and heteroaryl;
$R^5$ is independently selected from the group consisting of alkyl optionally substituted with OH or SH; cycloalkyl optionally substituted with halo; aryl; and heteroaryl; and
$R^6$ is independently selected from sulfonyl.

In a second aspect, the present application provides a process for the preparation of a compound of Formula I, comprising the steps of:
  i) reacting a compound of Formula A with $R^5NH_2$ and $R^6Cl$ in the presence of a base to form a compound of Formula B, and
  ii) reacting the compound of Formula B in the presence of a base to form the compound of Formula I,
  wherein the reaction of step ii) is carried out at a temperature higher than a reaction temperature of step i);

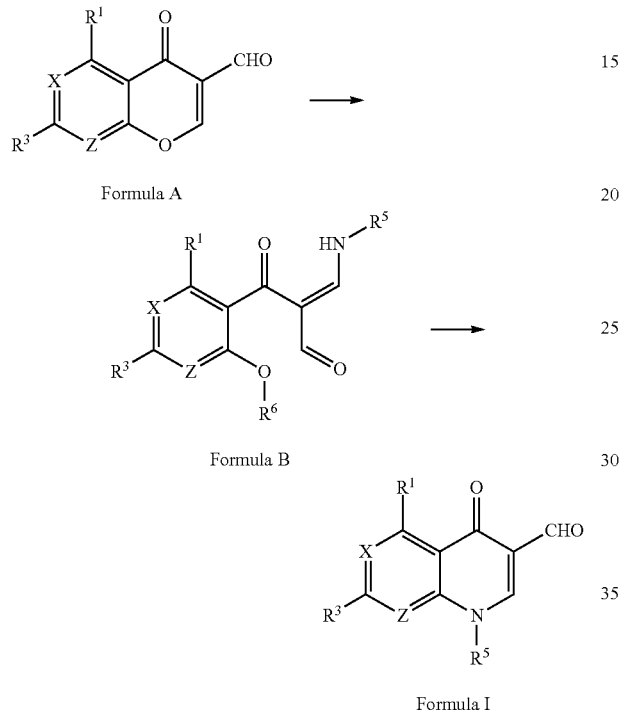

wherein:
X is selected from the group consisting of $CR^2$ and N;
Z is selected from the group consisting of $CR^4$ and N;
$R^1$ is independently selected from the group consisting of hydrogen, alkyl, alkoxy, halo, $NO_2$, CN, optionally substituted amino, haloalkyl, aryl, and heteroaryl;
$R^2$ and $R^3$ are each independently selected from the group consisting of hydrogen, alkyl, alkoxy, halo, amino, $NO_2$, CN, haloalkyl, aryl, and heteroaryl; or $R^2$ and $R^3$ are linked together to form a ring;
$R^4$ is independently selected from the group consisting of hydrogen, alkyl, alkoxy, halo, amino, $NO_2$, CN, haloalkyl, aryl, and heteroaryl;
$R^5$ is independently selected from the group consisting of alkyl optionally substituted with OH or SH; cycloalkyl optionally substituted with halo; aryl; and heteroaryl; and
$R^6$ is independently selected from sulfonyl.

In a third aspect, the present application provides a process for the preparation of a compound of Formula II, comprising the steps of:
  preparing a compound of Formula I according to the process of the first aspect or the process of the second aspect described above; and
  oxidizing the compound of Formula I to generate the compound of Formula II,

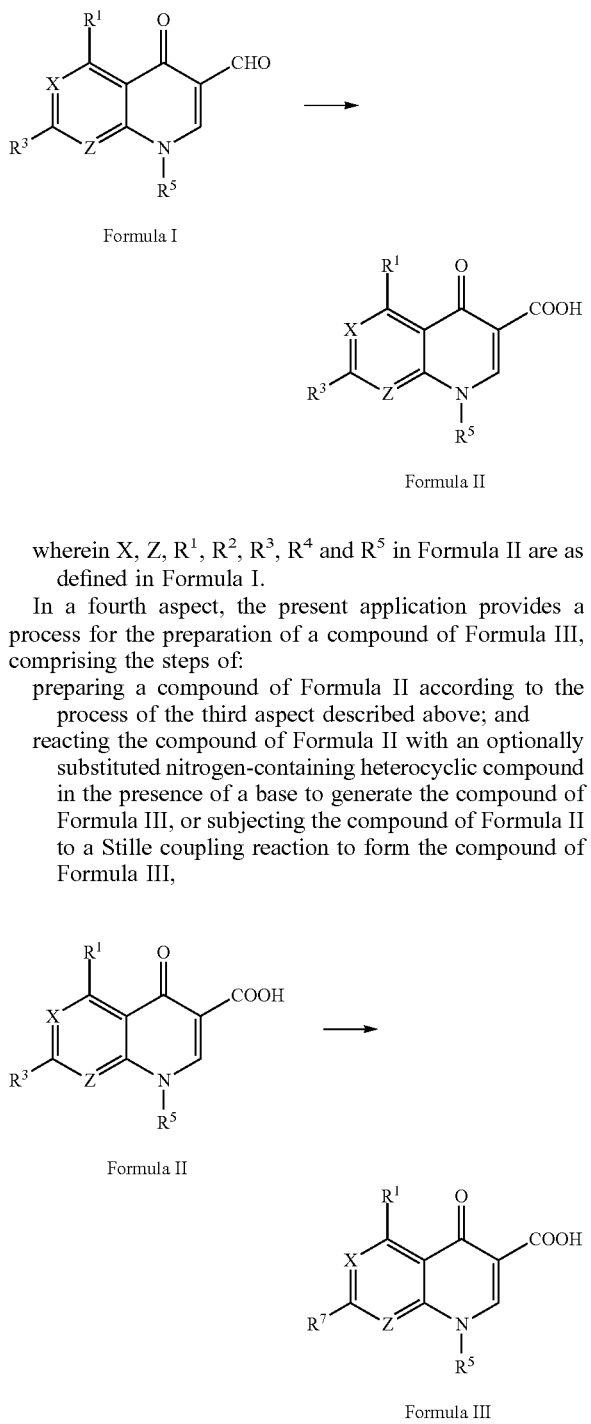

wherein X, Z, $R^1$, $R^2$, $R^3$, $R^4$ and $R^5$ in Formula II are as defined in Formula I.

In a fourth aspect, the present application provides a process for the preparation of a compound of Formula III, comprising the steps of:
  preparing a compound of Formula II according to the process of the third aspect described above; and
  reacting the compound of Formula II with an optionally substituted nitrogen-containing heterocyclic compound in the presence of a base to generate the compound of Formula III, or subjecting the compound of Formula II to a Stille coupling reaction to form the compound of Formula III, wherein:
in Formula II, $R^2$ and $R^3$ do not form a ring, and $R^3$ is halo;
in Formula III, X, Z, $R^1$, $R^2$, $R^4$, and $R^5$ are as defined in Formula II, and $R^7$ is selected from the group consisting of optionally substituted N-heterocyclyl, optionally substituted heteroaryl, and optionally substituted aryl.

In a fifth aspect, the present application provides a process for the preparation of a compound of Formula IV, comprising the steps of:
  preparing a compound of Formula II according to the process of the third aspect described above; and reacting the compound of Formula II under a suitable condition to generate the compound of Formula IV,

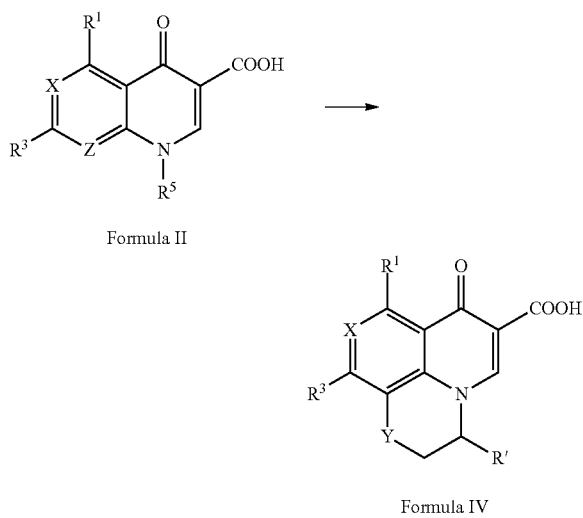

Formula II

Formula IV wherein in Formula II, Z is CR$^4$, R$^4$ is halo or amino, and R$^6$ is alkyl substituted with OH or SH;
wherein in Formula IV, X, R, R$^2$ and R$^3$ are as defined in Formula II, Y is O or S, and R$^1$ is alkyl.

DETAILED DESCRIPTION

In a first aspect, the present application provides a process for the preparation of a compound of Formula I, comprising the steps of:
reacting a compound of Formula A with R$^5$NH$_2$ and R$^6$Cl in the presence of a base to form the compound of Formula I,

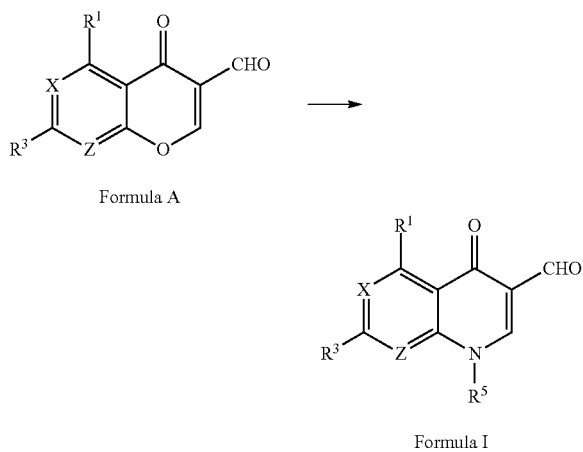

Formula A

Formula I wherein:
X is selected from the group consisting of CR$^2$ and N;
Z is selected from the group consisting of CR$^4$ and N;
R$^1$ is independently selected from the group consisting of hydrogen, alkyl, alkoxy, halo, NO$_2$, CN, optionally substituted amino, haloalkyl, aryl, and heteroaryl;
R$^2$ and R$^3$ are each independently selected from the group consisting of hydrogen, alkyl, alkoxy, halo, amino, N$_2$, CN, haloalkyl, aryl, and heteroaryl; or R$^2$ and R$^3$ are linked together to form a ring;

R$^4$ is independently selected from the group consisting of hydrogen, alkyl, alkoxy, halo, amino, NO$_2$, CN, haloalkyl, aryl, and heteroaryl;
R$^5$ is independently selected from the group consisting of alkyl optionally substituted with OH or SH; cycloalkyl optionally substituted with halo; aryl; and heteroaryl; and
R$^6$ is independently selected from sulfonyl.

In some embodiments, the base is selected from the group consisting of inorganic bases, organic bases, and combinations thereof.

In some embodiments, the base is selected from primary amines.

In some embodiments, the base is selected from the group consisting of potassium carbonate, cesium carbonate, sodium carbonate, sodium hydroxide, lithium tert-butoxide, sodium methoxide, sodium bicarbonate, sodium hydride, triethylamine, diisopropylamine, 1,8-diazabicyclo[5.4.0]undec-7-ene (DBU), 1,4-diazabicyclo[2.2.2]octane (DABCO), and combinations thereof.

In some embodiments, the base is selected from the group consisting of potassium carbonate, cesium carbonate, sodium carbonate, and combinations thereof.

In some embodiments, the reaction is carried out in a solvent.

In some embodiments, the reaction is carried out in a solvent selected from the group consisting of methanol, ethanol, acetonitrile, toluene, water, N,N-dimethylformamide, xylene, nitrobenzene, trifluorotoluene, N-methylpyrrolidone, 1,2-dichloroethane, 1,4-dioxane, and combinations thereof.

In some embodiments, the reaction is carried out in a solvent selected from the group consisting of N,N-dimethylformamide, N-methylpyrrolidone, and a combination thereof.

In some embodiments, the reaction is carried out at a temperature of 80° C.-200° C. (e.g., 80° C., 90° C., 100° C., 110° C., 120° C., 130° C., 140° C., 150° C., 160° C., 170° C., 180° C., 190° C., or 200° C.) or 100° C.-150° C.

In a second aspect, the present application provides a process for the preparation of a compound of Formula I, comprising the steps of:
i) reacting a compound of Formula A with R$^5$NH$_2$ and R$^6$Cl in the presence of a base to form a compound of Formula B, and
ii) reacting the compound of Formula B in the presence of a base to form the compound of Formula I,
wherein the reaction of step ii) is carried out at a temperature higher than a reaction temperature of step i);

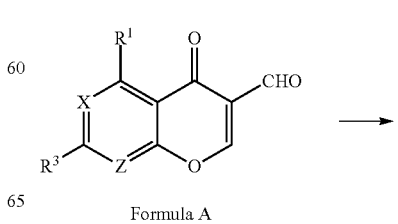

Formula A

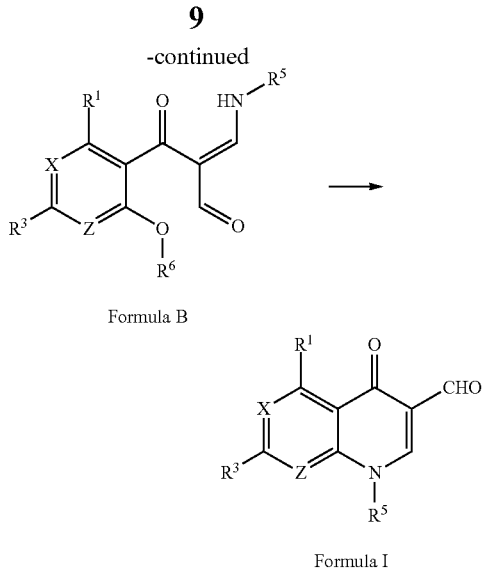

Formula B

Formula I wherein:

X is selected from the group consisting of $CR^2$ and N;
Z is selected from the group consisting of $CR^4$ and N;
$R^1$ is independently selected from the group consisting of hydrogen, alkyl, alkoxy, halo, $NO_2$, CN, optionally substituted amino, haloalkyl, aryl, and heteroaryl;
$R^2$ and $R^3$ are each independently selected from the group consisting of hydrogen, alkyl, alkoxy, halo, amino, $NO_2$, CN, haloalkyl, aryl, and heteroaryl; or $R^2$ and $R^3$ are linked together to form a ring;
$R^4$ is independently selected from the group consisting of hydrogen, alkyl, alkoxy, halo, amino, $NO_2$, CN, haloalkyl, aryl, and heteroaryl;
$R^5$ is independently selected from the group consisting of alkyl optionally substituted with OH or SH; cycloalkyl optionally substituted with halo; aryl; and heteroaryl; and
$R^6$ is independently selected from sulfonyl.

In some embodiments, the base in step i) is selected from the group consisting of inorganic bases, organic bases, and combinations thereof. In some embodiments, the base in step i) is selected from primary amines, preferably excess primary amines.

In some embodiments, the base in step i) is selected from the group consisting of potassium carbonate, cesium carbonate, sodium carbonate, sodium hydroxide, lithium tert-butoxide, sodium methoxide, sodium bicarbonate, sodium hydride, triethylamine, diisopropylamine, 1,8-diazabicyclo[5.4.0]undec-7-ene, 1,4-diazabicyclo[2.2.2]octane, and combinations thereof.

In some embodiments, the base in step i) is selected from the group consisting of lithium tert-butoxide, potassium carbonate, cesium carbonate, sodium carbonate, sodium bicarbonate, triethylamine, diisopropylamine, 1,8-diazabicyclo[5.4.0]undec-7-ene, and combinations thereof.

In some embodiments, the reaction of step i) is carried out in a first solvent.

In some embodiments, the reaction of step i) is carried out in a first solvent selected from the group consisting of methanol, ethanol, acetonitrile, toluene, water, dimethyl sulfoxide, N,N-dimethylformamide, 1,4-dioxane, and combinations thereof.

In some embodiments, the reaction of step i) is carried out at a temperature ranging from room temperature to 150° C. (e.g., 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., or 150° C.) or from room temperature to 100° C.

In some embodiments, the base in step ii) is selected from inorganic bases.

In some embodiments, the base in step ii) is selected from the group consisting of potassium carbonate, cesium carbonate, sodium carbonate, sodium hydroxide, lithium tert-butoxide, sodium methoxide, sodium bicarbonate, sodium hydride, and combinations thereof.

In some embodiments, the base in step ii) is selected from the group consisting of potassium carbonate, cesium carbonate, sodium carbonate, and combinations thereof.

In some embodiments, the reaction of step ii) is carried out in a second solvent, wherein the second solvent and the first solvent may be the same or different.

In some embodiments, the reaction of step ii) is carried out in a second solvent selected from the group consisting of xylene, nitrobenzene, trifluorotoluene, 1,2-dichloroethane, acetonitrile, toluene, dimethylsulfoxide, N,N-dimethylformamide, 1,4-dioxane, N-methylpyrrolidone, and combinations thereof.

In some embodiments, the reaction of step ii) is carried out in a second solvent selected from the group consisting of N-methylpyrrolidone, N,N-dimethylformamide, and a combination thereof.

In some embodiments, the reaction of step ii) is carried out at a temperature of 100° C.-200° C. (e.g., 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., or 200° C.) or 100° C.-150° C.

In some embodiments, X is selected from $CR^2$.
In some embodiments, X is selected from N.
In some embodiments, Z is selected from $CR^4$.
In some embodiments, Z is selected from N.
In some embodiments, $R^1$ is independently selected from the group consisting of hydrogen, $C_{1-6}$ alkyl, $C_{1-6}$ alkoxy, halo, $NO_2$, CN, optionally substituted amino, $C_{1-6}$ haloalkyl, $C_{6-12}$ aryl, and $C_{2-12}$ heteroaryl.
In some embodiments, $R^1$ is independently selected from the group consisting of hydrogen, $C_{1-4}$ alkyl, $C_{1-4}$ alkoxy, halo, $NO_2$, CN, optionally substituted amino, $C_{1-4}$ haloalkyl, $C_{6-10}$ aryl, and $C_{2-10}$ heteroaryl.
In some embodiments, $R^6$ is independently selected from the group consisting of hydrogen, alkyl, and amino.
In some embodiments, $R^6$ is independently selected from the group consisting of hydrogen, and alkyl.
In some embodiments, $R^6$ is independently selected from the group consisting of hydrogen, methyl, methoxy, F, Cl, Br, I, $NO_2$, CN, $CF_3$, and amino.
In some embodiments, $R^1$ is independently selected from the group consisting of hydrogen, methyl, and amino.
In some embodiments, $R^1$ is independently selected from the group consisting of hydrogen, and methyl.
In some embodiments, $R^2$ and $R^3$ are each independently selected from the group consisting of hydrogen, $C_{1-6}$ alkyl, $C_{1-6}$ alkoxy, halo, amino, $NO_2$, CN, $C_{1-6}$ haloalkyl, $C_{6-12}$ aryl, and $C_{2-12}$ heteroaryl.
In some embodiments, $R^2$ and $R^3$ are linked together to form a 3- to 12-membered ring, e.g., a 5- to 12-membered non-aromatic heterocycle.
In some embodiments, $R^2$ and $R^3$ are each independently selected from the group consisting of hydrogen, $C_{1-4}$ alkyl, $C_{1-4}$ alkoxy, halo, amino, $NO_2$, CN, $C_{1-4}$ haloalkyl, $C_{6-10}$ aryl, and $C_{2-10}$ heteroaryl.

In some embodiments, $R^2$ and $R^3$ are linked together to form a 5- to 10-membered ring, e.g., a 5- to 10-membered non-aromatic heterocycle.

In some embodiments, $R^2$ and $R^3$ are each independently selected from the group consisting of hydrogen, methyl, methoxy, F, Cl, Br, I, amino, $NO_2$, CN, and $CF_3$.

In some embodiments, $R^2$ and $R^3$ are each independently selected from the group consisting of hydrogen, halo, and amino.

In some embodiments, $R^2$ and $R^3$ are each independently selected from the group consisting of hydrogen, and halo.

In some embodiments, $R^2$ and $R^3$ form a 5- to 7-membered non-aromatic heterocycle, such as 1,3-dioxole.

In some embodiments, $R^4$ is independently selected from the group consisting of hydrogen, $C_{1-6}$ alkyl, $C_{1-6}$ alkoxy, halo, amino, $NO_2$, CN, $C_{1-6}$ haloalkyl, $C_{6-12}$ aryl, and $C_{2-12}$ heteroaryl.

In some embodiments, $R^4$ is independently selected from the group consisting of hydrogen, $C_{1-4}$ alkyl, $C_{1-4}$ alkoxy, halo, amino, $NO_2$, CN, $C_{1-4}$ haloalkyl, $C_{6-10}$ aryl, and $C_{2-10}$ heteroaryl.

In some embodiments, $R^4$ is independently selected from the group consisting of hydrogen, alkyl, alkoxy, halo, amino, and CN.

In some embodiments, $R^4$ is independently selected from the group consisting of hydrogen, alkyl, alkoxy, halo, amino, and CN.

In some embodiments, $R^4$ is independently selected from the group consisting of hydrogen, methyl, methoxy, F, Cl, Br, I, $NH_2$, $NO_2$, CN, and $CF_3$.

In some embodiments, $R^4$ is independently selected from the group consisting of hydrogen, methyl, methoxy, F, Cl, $NH_2$, and CN.

In some embodiments, $R^4$ is independently selected from the group consisting of hydrogen, methyl, methoxy, F, Cl, and CN.

In some embodiments, $R^4$ is independently selected from halo or amino.

In some embodiments, $R^4$ is independently selected from halo.

In some embodiments, $R^5$ is independently selected from the group consisting of hydrogen; $C_{1-6}$ alkyl optionally substituted with OH or SH; 3- to 12-membered cycloalkyl optionally substituted with halo; $C_{6-12}$ aryl; and $C_{2-12}$ heteroaryl.

In some embodiments, $R^1$ is independently selected from the group consisting of $C_{1-6}$ alkyl optionally substituted with OH or SH; 3- to 12-membered cycloalkyl optionally substituted with halo; $C_{6-12}$ aryl; and $C_{2-12}$ heteroaryl.

In some embodiments, $R^6$ is independently selected from hydrogen; $C_{1-4}$ alkyl optionally substituted with OH or SH; 3- to 8-membered cycloalkyl optionally substituted with halo; $C_{6-10}$ aryl; and $C_{2-10}$ heteroaryl.

In some embodiments, $R^1$ is independently selected from the group consisting of hydrogen; alkyl optionally substituted with OH or SH; and cycloalkyl optionally substituted with halo.

In some embodiments, $R^5$ is independently selected from the group consisting of alkyl optionally substituted with OH or SH, and cycloalkyl optionally substituted with halo.

In some embodiments, $R^5$ is independently selected from the group consisting of hydrogen, ethyl, cyclopropyl, fluorocyclopropyl, tert-butyl, —$(CH_2)_2OH$, —$(CH_2)_2SH$, —$CH(CH_3)CH_2OH$, and —$CH(CH_3)CH_2SH$.

In some embodiments, $R^5$ is independently selected from the group consisting of ethyl, cyclopropyl, fluorocyclopropyl, tert-butyl, —$(CH_2)_2SH$, and —$CH(CH_3)CH_2OH$.

In some embodiments, $R^5$ is independently selected from the group consisting of ethyl, cyclopropyl, fluorocyclopropyl, and tert-butyl.

In some embodiments, $R^6$ is independently selected from the group consisting of p-toluenesulfonyl and ethylsulfonyl.

In some embodiments, the halo is selected from the group consisting of F, Cl, Br, and I.

In some embodiments, at least one of $R^2$ and $R^3$ is halo.

In some embodiments, $R^3$ is halo.

In some embodiments, the compound of Formula I is selected from the group consisting of:

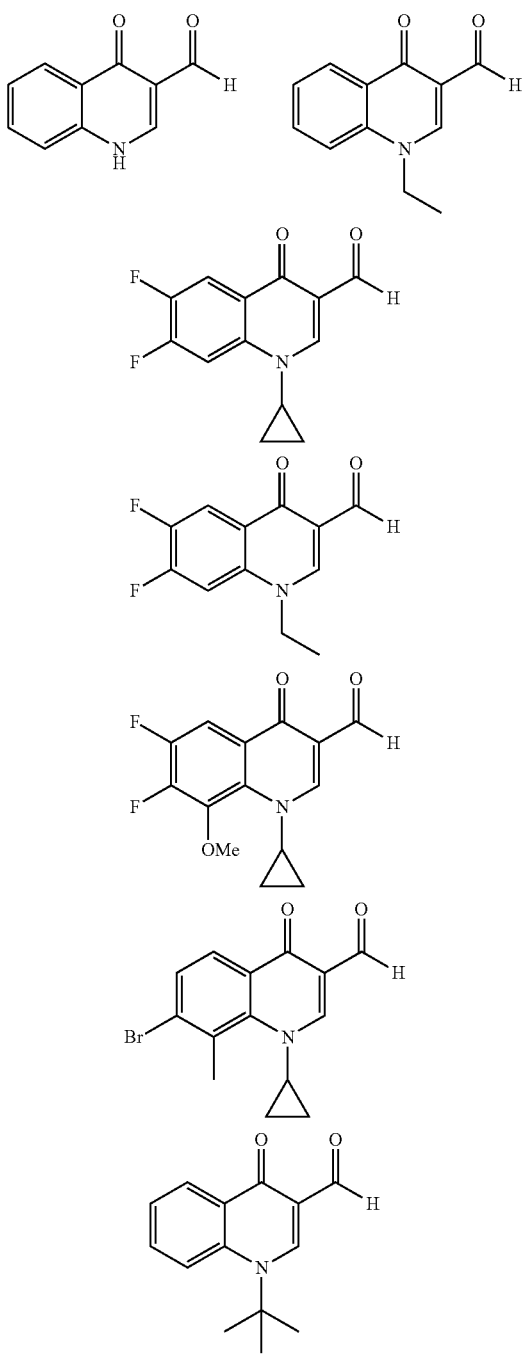

-continued

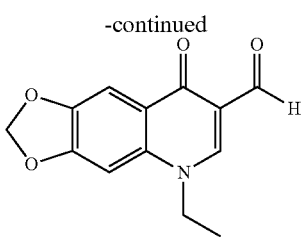
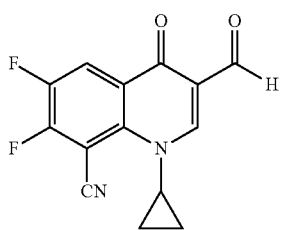
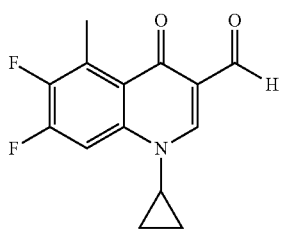
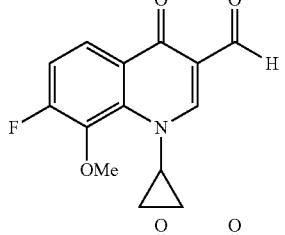
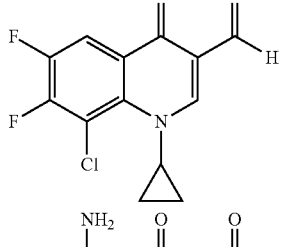
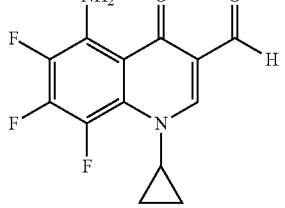
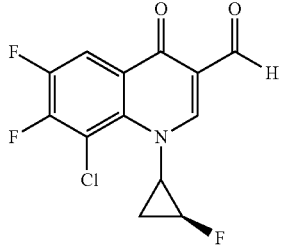

-continued

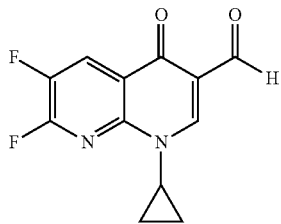
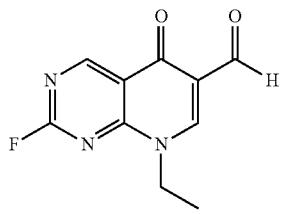
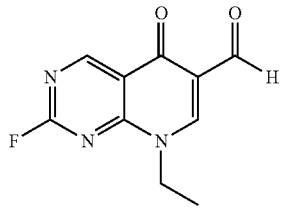
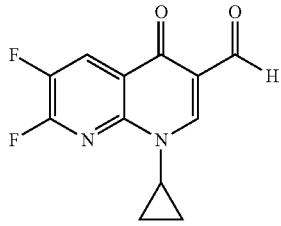
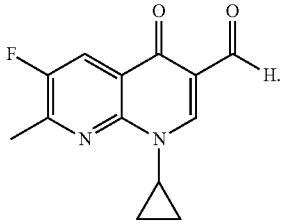

In a third aspect, the present application provides a process for the preparation of a compound of Formula II, comprising the steps of:

preparing a compound of Formula I according to the process of the first aspect or the process of the second aspect described above; and oxidizing the compound of Formula I to generate the compound of Formula II,

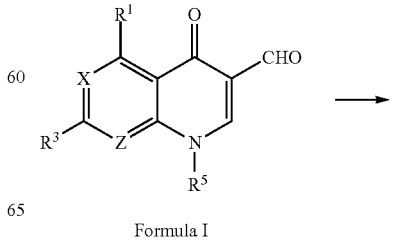

Formula I

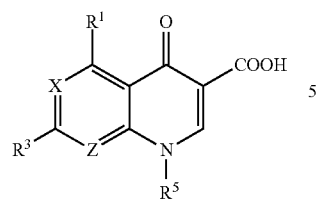

Formula II wherein X, Z, $R^1$, $R^2$, $R^3$, $R^4$ and $R^5$ in Formula II are as defined in Formula I.

In some embodiments, the oxidation is carried out in the presence of an oxidant selected from the group consisting of potassium permanganate, sodium chlorite/sulfamic acid, potassium peroxymonosulfate, trichloroisocyanuric acid/TEMPO, manganese dioxide, sodium hypochlorite, hydrogen peroxide, sodium bromate, and combinations thereof.

In some embodiments, the compound of Formula II is selected from the group consisting of:

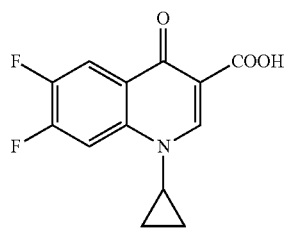

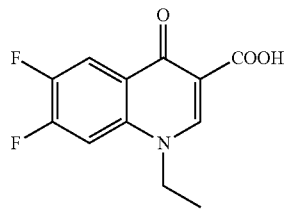

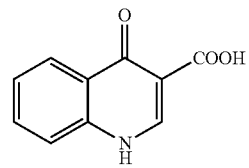

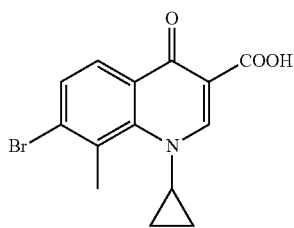

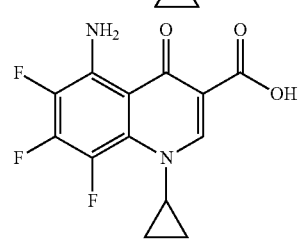

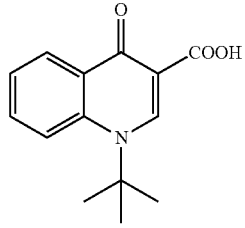

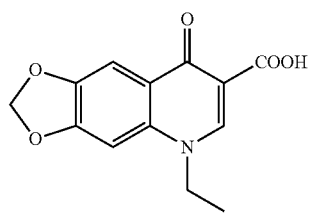

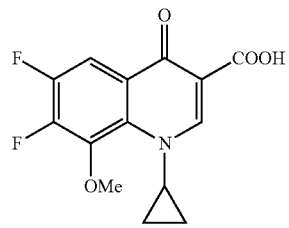

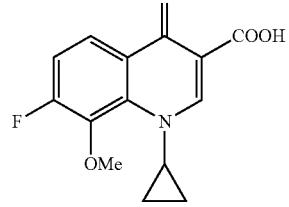

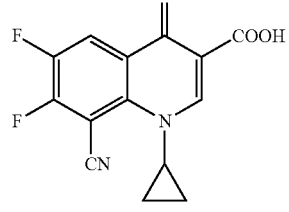

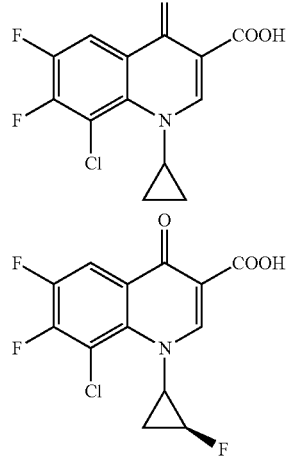

-continued

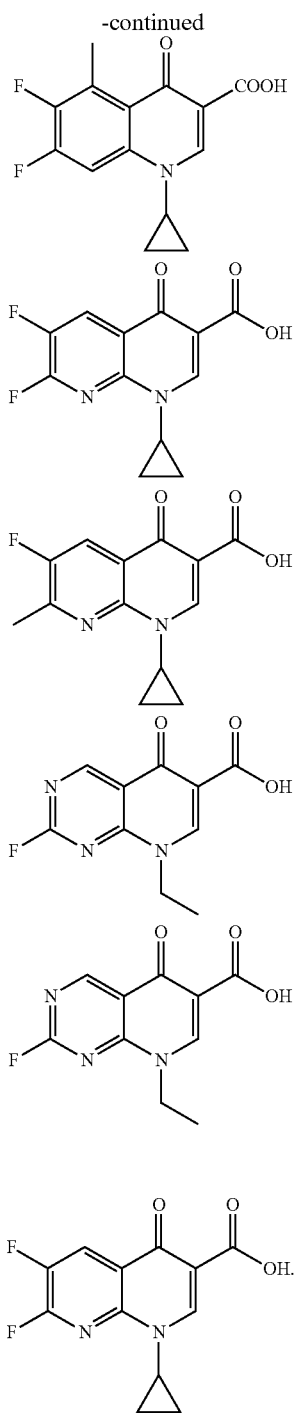

In a fourth aspect, the present application provides a process for the preparation of a compound of Formula III, comprising the steps of
preparing a compound of Formula II according to the process of the third aspect described above; and
reacting the compound of Formula II with an optionally substituted nitrogen-containing heterocyclic compound in the presence of a base to generate the compound of Formula III, or subjecting the compound of Formula II to a Stille coupling reaction to form the compound of Formula III, Formula I Formula III wherein:
in Formula II, $R^2$ and $R^3$ do not form a ring, and $R^3$ is halo; preferably $R^3$ is bromo or chloro;
in Formula III, X, Z, $R^1$, $R^2$, $R^4$, and $R^5$ are as defined in Formula II, and $R^7$ is selected from the group consisting of optionally substituted N-heterocyclyl, optionally substituted heteroaryl, and optionally substituted aryl. It will be appreciated by those skilled in the art that reacting a compound of Formula II with an optionally substituted nitrogen-containing heterocyclic compound in the presence of a base may produce a compound of Formula III wherein $R^6$ is selected from optionally substituted N-heterocyclyl. When it is desired to prepare a compound of Formula III wherein $R^1$ is selected from optionally substituted heteroaryl or optionally substituted aryl, the compound of Formula III wherein $R^7$ is selected from optionally substituted heteroaryl or optionally substituted aryl may be generated by subjecting the compound of Formula II to a Stille coupling reaction.

In some embodiments, the optionally substituted nitrogen-containing heterocyclic compound is selected from nitrogen-containing heterocyclic compounds optionally substituted with one or more substituents selected from the group consisting of alkyl optionally substituted with $NH_2$; =N(alkoxy); alkoxy; cycloalkyl; hydroxy; and optionally substituted amino.

In some embodiments, the optionally substituted nitrogen-containing heterocyclic compound is selected from the group consisting of piperidine, piperazine, tetrahydropyrrole, pyrrolomorpholine, pyrrolopiperidine, azaspiro[2.4]heptane, and azepane, each optionally substituted with one or more substituents selected from the group consisting of $C_{1-6}$ alkyl optionally substituted with $NH_2$; =N($C_{1-6}$ alkoxy); $C_{1-6}$ alkoxy; 3- to 7-membered cycloalkyl; hydroxy; and $NH_2$; wherein said $NH_2$ is optionally substituted with one or more groups selected from $C_{1-6}$ alkyl.

In some embodiments, $R^7$ is selected from the group consisting of N-heterocyclyl, heteroaryl, and aryl, each optionally substituted with one or more substituents selected from the group consisting of alkyl optionally substituted with $NH_2$; =N(alkoxy); alkoxy; cycloalkyl; hydroxy; alkylamido optionally substituted with alkyl; and optionally substituted amino.

In some embodiments, $R^7$ is selected from the group consisting of 5- to 12-membered N-heterocyclyl, $C_{2-12}$ heteroaryl, and $C_{6-12}$ aryl, each optionally substituted with one or more substituents selected from the group consisting of $C_{1-6}$ alkyl optionally substituted with $NH_2$; $=N(C_{1-6}$ alkoxy); $C_{1-6}$ alkoxy; 3- to 7-membered cycloalkyl; hydroxy; $C_{1-6}$ alkylamido optionally substituted with $C_{1-6}$ alkyl; and $NH_2$ optionally substituted with one or more $C_{1-6}$ alkyl.

In some embodiments, $R^7$ is selected from 5- to 12-membered N-heterocyclyl optionally substituted with one or more substituents selected from the group consisting of $C_{1-6}$ alkyl optionally substituted with $NH_2$; $=N(C_{1-6}$ alkoxy); 3- to 7-membered cycloalkyl; hydroxy; and $NH_2$ optionally substituted with one or more $C_{1-6}$ alkyl.

In some embodiments, $R^7$ is selected from $C_{2-12}$ heteroaryl (e.g., pyridyl) optionally substituted with one or more substituents selected from the group consisting of $C_{1-6}$ alkyl; $C_{1-6}$ alkylamido optionally substituted with $C_{1-6}$ alkyl; and $NH_2$ optionally substituted with one or more $C_{1-6}$ alkyl.

In some embodiments, the N-heterocyclyl is N-heterocycloalkyl.

In some embodiments, $R^7$ is selected from the group consisting of:

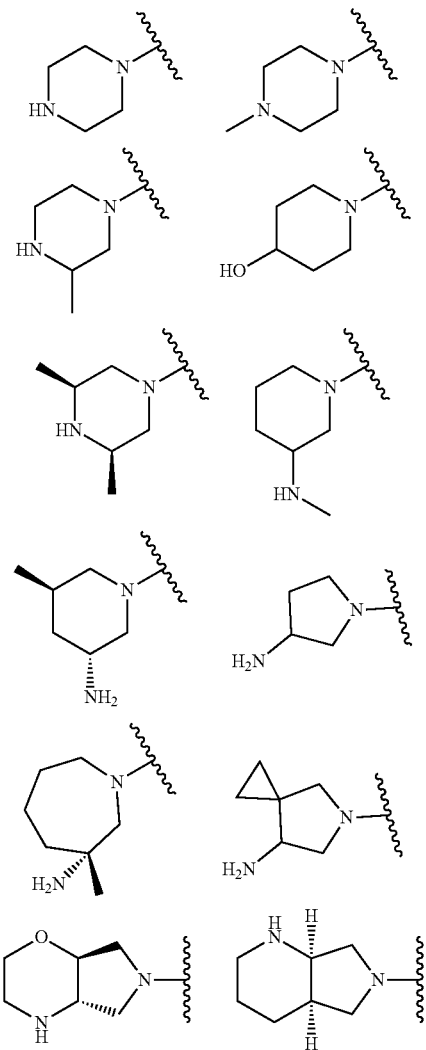

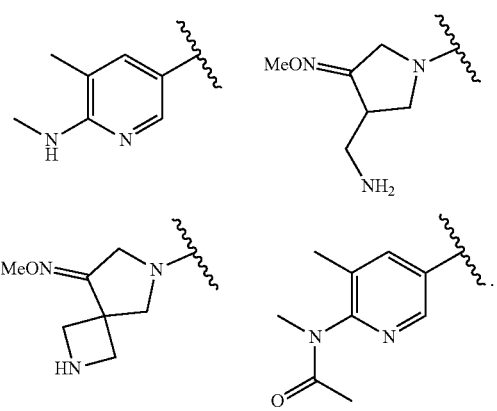

In some embodiments, the compound of Formula III is selected from the group consisting of:

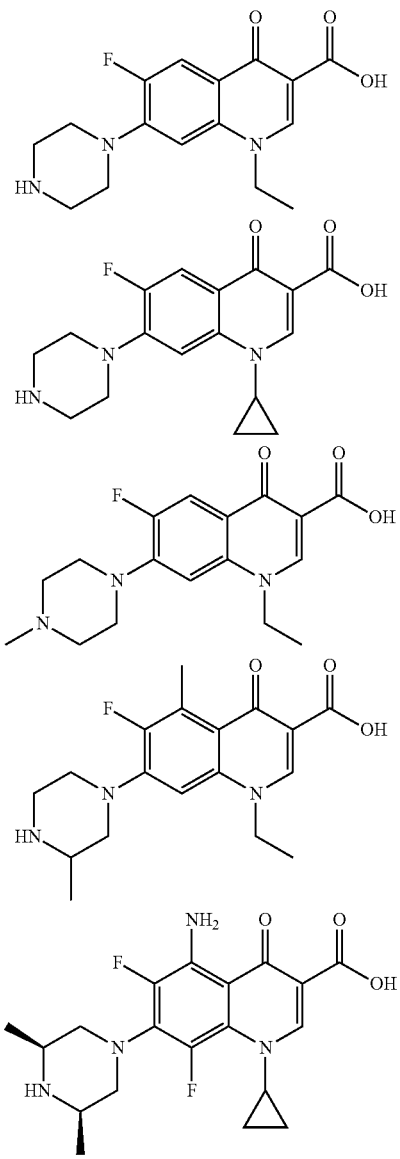

-continued
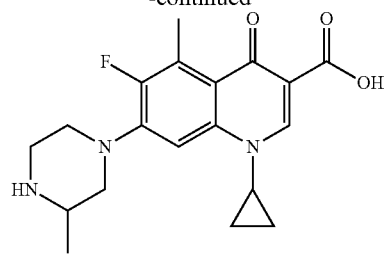
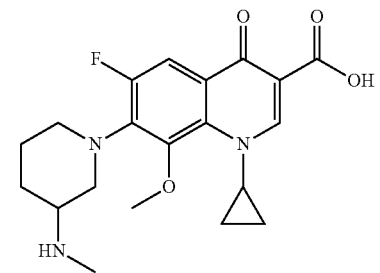
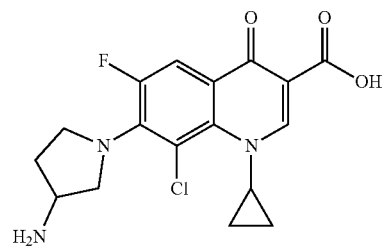
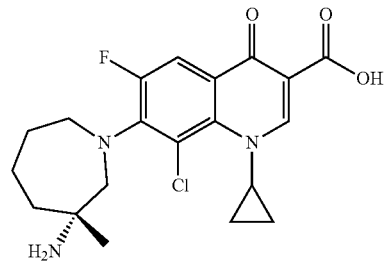
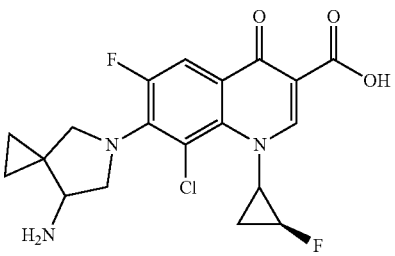
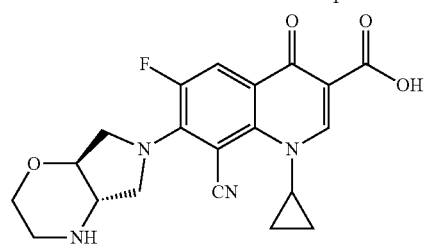
-continued
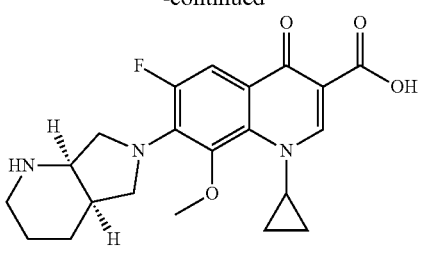
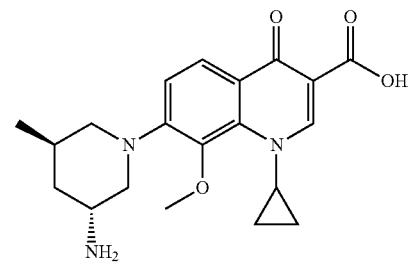
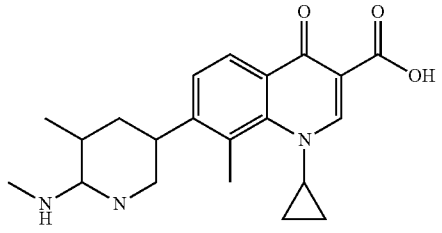
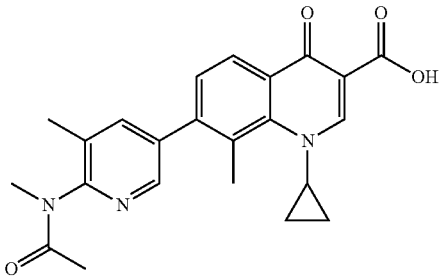
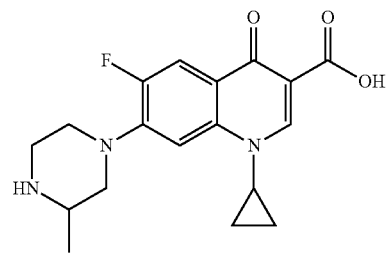
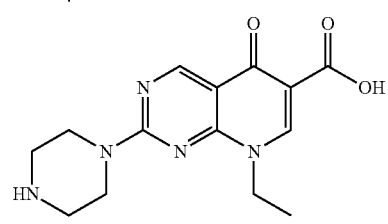
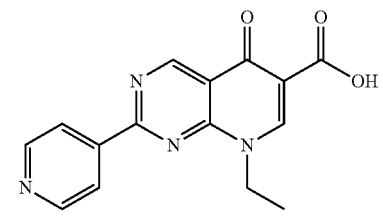

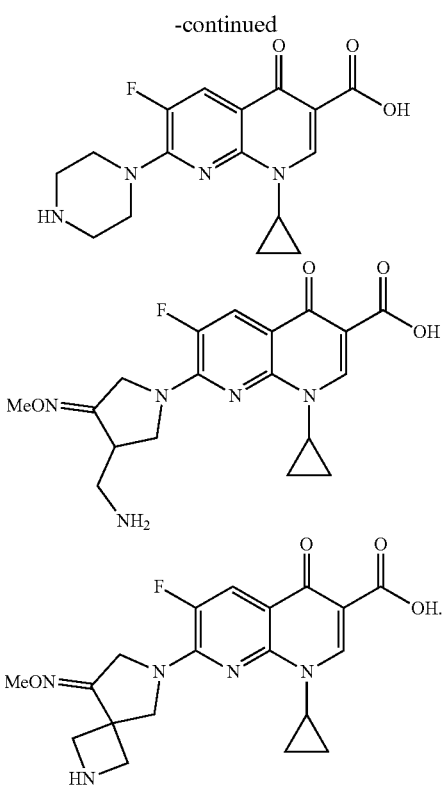

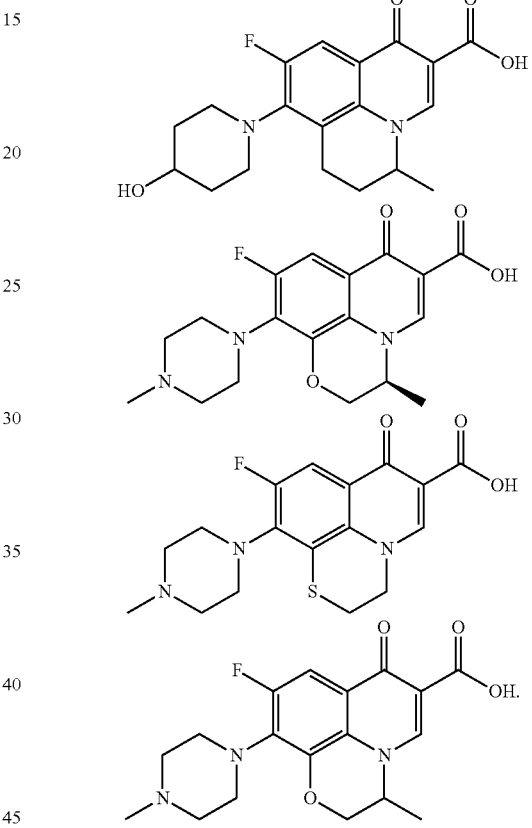

In a fifth aspect, the present application provides a process for the preparation of a compound of Formula IV, comprising the steps of:

preparing a compound of Formula II according to the process of the third aspect described above; and reacting the compound of Formula II under nucleophilic substitution conditions to generate the compound of Formula IV,

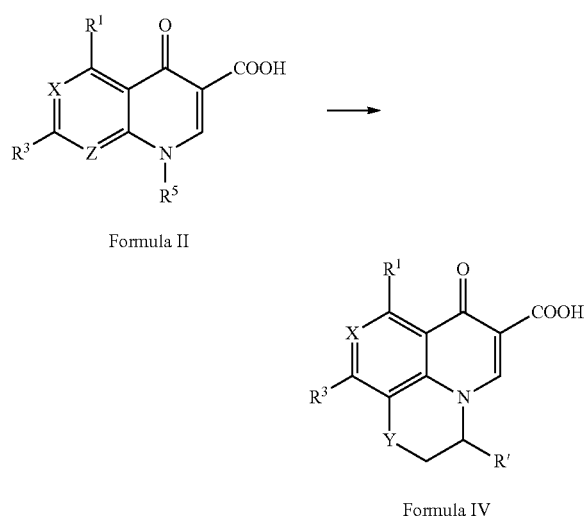

wherein in Formula II, Z is $CR^4$, $R^4$ is halo or amino, and $R^5$ is alkyl substituted with OH or SH;

wherein in Formula IV, X, R, $R^2$ and $R^3$ are as defined in Formula II, Y is O or S, and $R^1$ is alkyl.

In some embodiments, $R^4$ is fluoro.

In some embodiments, $R^5$ is $C_{1-6}$ alkyl substituted with OH or SH.

In some embodiments, $R^6$ is $C_{1-4}$ alkyl substituted with OH or SH.

In some embodiments, $R^5$ is ethyl or isopropyl each substituted with OH or SH.

In some embodiments, $R^1$ is $C_{1-6}$ alkyl.

In some embodiments, $R^1$ is $C_{1-4}$ alkyl.

In some embodiments, $R^1$ is ethyl or isopropyl.

In some embodiments the compound of Formula IV is selected from the group consisting of:

It is to be understood that the above-mentioned embodiments may be combined to form a technical solution comprising the features of the combined embodiments without conflict. Such combined solutions are within the scope of the present disclosure.

Definitions

The following definitions and methods are provided to better define the present application and to guide those of ordinary skill in the art in the practice of the present application. Unless otherwise indicated, terms are to be understood in accordance with conventional usage of those of ordinary skill in the relevant field.

The term "comprise" and English variations thereof (such as comprises or comprising) should be understood in an open and non-exclusive sense, i.e. "including but not limited to".

The term "optional" or "optionally" means that the subsequently described event or circumstance may or may not occur, and that the description includes instances where said event or circumstance occurs and instances where said event or circumstance does not occurs.

The oxidant "sodium chlorite/sulfamic acid" refers to an oxidant consisting of both sodium chlorite and sulfamic acid.

Where a range of numerical values is described herein, the range includes the endpoints thereof and all the individual integers and fractions within the range, and also includes each of narrower ranges therein formed by all the various possible combinations of those endpoints and internal integers and fractions, so as to form subgroups of larger groups of values within the stated range to the same extent as if each of those narrower ranges is explicitly described. For example, the expression that the reaction temperature is 80° C.-200° C. means that the reaction temperature may be, for example, 80° C., 90° C., 100° C., 110° C., 120° C., 130° C., 140° C., 150° C., 160° C., 170° C., 180° C., 190° C., or 200° C., etc., and ranges therebetween.

The numerical range herein indicating the number of carbon atoms refers to each of the integers within this given range. For example, "$C_1$-$C_{12}$" or "$C_{1-12}$" means that this group may have 1, 2, 3, 4, 5, 6, 7, 8, 9, 10, 11, 12 carbon atoms.

The term "membered" refers to the number of skeleton atoms constituting the ring. For example, "3- to 12-membered" means that the number of skeleton atoms constituting the ring is 3, 4, 5, 6, 7, 8, 9, 10, 11, or 12.

The term "halo" or "halogen" itself or as a part of another substituent refers to fluorine (F), chlorine (Cl), bromine (Br) or iodine (I) atom.

The term "alkyl" refers to a linear or branched saturated hydrocarbon group. Examples of alkyl include $C_{1-4}$ alkyl, $C_{1-6}$ alkyl, $C_{1-8}$ alkyl, $C_{1-10}$ alkyl, $C_{1-12}$ alkyl, and the like, such as methyl (Me), ethyl (Et), propyl (e.g., n-propyl and isopropyl), butyl (e.g., n-butyl, isobutyl, s-butyl, and t-butyl), pentyl (e.g., n-pentyl, isopentyl, and neopentyl), and the like. For example, the term "$C_{1-6}$ alkyl" refers to an alkyl group containing 1 to 6 (e.g., 1, 2, 3, 4, 5, or 6) carbon atoms (such as methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, and 2-methylpentyl, and the like).

The term "alkoxy" refers to —O-alkyl, wherein "alkyl" is defined as above, and examples of "alkoxy" include, but are not limited to, methoxy, ethoxy, n-propoxy, isopropoxy, n-butoxy, sec-butoxy, tert-butoxy, n-pentoxy, and isopentoxy. "Optionally substituted alkoxy" means that the alkyl group in the alkoxy group is substituted or unsubstituted.

The term "alkenyl" refers to a linear or branched unsaturated aliphatic hydrocarbon group having at least one double bond consisting of carbon atoms and hydrogen atoms, such as $C_{2-6}$ alkenyl, $C_{2-4}$ alkenyl, and the like. Non-limiting examples of alkenyl groups include, but are not limited to, ethenyl, 1-propenyl, 2-propenyl, 1-butenyl, isobutenyl, 1,3-butadienyl, and the like. This term includes cis- and trans-isomers or mixtures of these isomers.

The term "alkynyl" refers to a linear or branched unsaturated aliphatic hydrocarbon group having at least one triple bond consisting of carbon atoms and hydrogen atoms, such as $C_{2-6}$ alkynyl, $C_{2-4}$ alkynyl, $C_{2-3}$ alkynyl, and the like. Non-limiting examples of alkynyl groups include, but are not limited to, ethynyl (—C≡CH), 1-propynyl (—C≡C—CH$_3$), 2-propynyl (—CH$_2$—C≡CH), 1,3-butyldiynyl (—C≡C—C≡CH), and the like.

The term "cycloalkyl" refers to a fully saturated non-aromatic ring consisting of carbon atoms and hydrogen atoms, preferably comprising 1 or 2 rings. The cycloalkyl group may be a monocyclic, fused polycyclic, bridged cyclic or spirocyclic structure. Non-limiting examples of cycloalkyl include, but are not limited to, $C_{3-18}$ is cycloalkyl, $C_{3-16}$ cycloalkyl, $C_{3-12}$ cycloalkyl, $C_{3-10}$ cycloalkyl, $C_{3-8}$ cycloalkyl, $C_{3-7}$ cycloalkyl, $C_{3-6}$ cycloalkyl, etc., such as cyclopropyl, cyclobutyl, cyclopentyl, cyclohexyl, cycloheptyl, spiro [3.3]heptyl, norbornyl(bicyclo[2.2.1]heptyl), bicyclo[2.2.2]octyl, adamantyl, bicyclo[1.1.1]pent-1-yl, and the like.

The term "heterocycloalkyl" refers to a cyclic group that is fully saturated and may exist as a monocyclic, bridged cyclic or spirocyclic ring. Unless otherwise indicated, the heterocycle is typically a ring containing 1 to 5 (e.g., 1, 2, 3, 4, or 5) heteroatoms independently selected from sulfur, oxygen, and/or nitrogen. Examples of 3-membered heterocycloalkyl include, but are not limited to, oxiranyl, thiiranyl, and aziridinyl; non-limiting examples of 4-membered heterocycloalkyl include, but are not limited to, azetidinyl, oxetanyl, and thietanyl: examples of 5-membered heterocycloalkyl include, but are not limited to, tetrahydrofuranyl, tetrahydrothienyl, pyrrolidinyl, isoxazolidinyl, oxazolidinyl, isothiazolidinyl, thiazolidinyl, imidazolidinyl, and tetrahydropyrazolyl; examples of 6-membered heterocycloalkyl include, but are not limited to, piperidinyl, tetrahydropyranyl, tetrahydrothiopyranyl, morpholinyl, piperazinyl, 1,4-thioxanyl, 1,4-dioxanyl, thiomorpholinyl, 1,3-dithianyl and 1,4-dithianyl; and examples of 7-membered heterocycloalkyl include, but are not limited to, azepanyl, oxepanyl, and thiepanyl.

The term "N-heterocycloalkyl" refers to a group having the following structure:

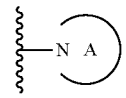

wherein ring A is a heterocycloalkyl ring as defined above comprising said nitrogen, i.e., a heterocycloalkyl comprising N as an attachment point.

Unless otherwise indicated, the term "heterocyclyl" or "heterocycle" refers to a cyclic structure that may be saturated or partially unsaturated, and non-aromatic, wherein the cyclic structure contains at least one carbon and at least one heteroatom (e.g., 1, 2, 3, 4, or 5 heteroatoms) selected from the group consisting of O, N, and S, and examples of heterocyclyl include heterocycloalkyl, heterocycloalkenyl, and heterocycloalkynyl.

The term "N-heterocyclyl" refers to a group having the following structure:

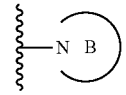

wherein ring B is a heterocyclyl ring as defined above comprising said nitrogen, namely, a heterocyclyl comprising N as an attachment point. 5- to 12-membered N-heterocyclyl is a heterocyclyl containing, for example, 5, 6, 7, 8, 9, 10, 11, or 12 ring-forming atoms. "Optionally substituted N-heterocyclyl" means that the heterocyclyl moiety in this group is substituted or unsubstituted.

The term "nitrogen-containing heterocyclic compound" refers to a compound comprising or consisting of a heterocyclic ring as defined above containing nitrogen as a ring-forming atom.

The term "cycloalkenyl" refers to a non-aromatic monocyclic or polycyclic ring system containing at least one carbon-carbon double bond. In some embodiments, the cycloalkenyl ring contains, for example, 3-10 ring atoms, 5 to 10 ring atoms, or 5 to 7 ring atoms. Non-limiting examples of suitable monocyclic cycloalkenyl include cyclo pentenyl, cyclohexenyl, cycloheptenyl, etc. A non-limiting example of a suitable polycyclic cycloalkenyl is norbornenyl.

The term "heterocycloalkenyl" refers to a non-aromatic monocyclic or polycyclic ring system containing at least one carbon-carbon or carbon-nitrogen double bond and consisting solely of carbon and hydrogen atoms, wherein one or more ring atoms in the ring system are elements in addition to carbon. For example, 1, 2, 3, 4, or 5 ring atoms are each independently heteroatoms selected from the group consisting of nitrogen, oxygen, and sulfur. There are no adjacent oxygen and/or sulfur atoms in the ring system. In some embodiments, the heterocycloalkenyl ring contains, for example, 5 to 10 ring atoms, 5 to 8 ring atoms, 5 to 7 ring atoms, or 5 to 6 ring atoms. The prefix "aza, oxa or thia" before the heterocycloalkenyl root name means that at least one nitrogen, oxygen or sulfur atom is present as a ring atom, respectively. Non-limiting examples of suitable monocyclic azacycloalkenyl groups include 1,2,3,4-tetrahydropyridinyl, 1,2-dihydropyridyl, 1,4-dihydropyridyl, 1,2,3, 6-tetrahydropyridinyl, 1,4,5,6-tetrahydropyrimidinyl, 2-pyrrolidinyl, 3-pyrrolidinyl, 2-imidazolinyl, 2-pyrazolinyl, and the like. Non-limiting examples of suitable oxacycloalkenyl groups include 3,4-dihydro-2H-pyran, dihydrofuranyl, fluorodihydrofuranyl, and the like. Non-limiting example of a suitable polycyclic oxacycloalkenyl group is 7-oxabicyclo [2.2.1]heptenyl.

The term "cycloalkynyl" refers to a non-aromatic monocyclic or polycyclic ring having at least one carbon-carbon triple bond and consisting solely of carbon and hydrogen atoms, for example a 4- to 15-membered, 5- to 15-membered, 6- to 10-membered, 7- to 10-membered or 8- to 10-membered ring, such as a 8- to 10-membered monocyclic ring or 12- to 15-membered bicyclic ring. It may comprise one or more fused or bridged rings. Unless otherwise stated, the cycloalkynyl ring may be attached at any carbon atom, which results in a stable structure, and if substituted, it may be substituted at any suitable carbon atom, which results in a stable structure. Exemplary cycloalkynyl groups include cyclooctynyl, cyclononenyl, cyclodecenyl, 2-methylcyclooctynyl, and the like.

The term "heterocycloalkynyl" means that at least one carbon-carbon single bond in a heterocycloalkyl group is replaced with one carbon-carbon triple bond.

The term "aryl" or "aromatic ring" refers to an aromatic ring or an aromatic or partially aromatic ring system consisting of a carbon atom and a hydrogen atom. It may be a monocyclic or polycyclic ring (e.g., two or more rings, such as bicyclic ring) where the rings are fused together or covalently linked. Non-limiting examples of aryl include, but are not limited to, phenyl, naphthyl, anthracenyl, and 1,2,3,4-tetrahydronaphthyl, and the like. Depending on the structure, the aryl group may be a monovalent group or a divalent group, i.e., an arylene group.

The term "$C_6$-$C_{18}$ aryl" or "aromatic ring" refers to an aryl or aromatic ring as defined above having 6 to 18 carbon atoms (e.g., 6, 7, 8, 9, 10, 11, 12, 13, 14, 15, 16, 17 or 18 carbon atoms).

"Heteroaryl" or "heteroaromatic ring" refers to an aromatic cyclic group consisting of carbon atoms and at least one (e.g., 1 to 5, such as 1, 2, 3, 4, or 5) heteroatom selected from the group consisting of nitrogen, oxygen, and sulfur. The heteroaryl group may be a monocyclic, bicyclic, tricyclic or tetracyclic ring system, which may comprise fused or bridged ring systems. Moreover, the nitrogen, carbon or sulphur atom in the heteroaryl group may be optionally oxidized, and the nitrogen atom may be optionally quaternized. Examples of heteroaryl groups include, but are not limited to, azepinyl, acridinyl, benzimidazolyl, benzothiazolyl, benzindolyl, benzothiadiazolyl, benzonaphthofuranyl, benzoxazolyl, benzodioxolyl, benzodioxinyl, benzopyranyl, benzopyronyl, benzofuranyl, benzofuranonyl, benzothiophenyl, benzotriazolyl, benzo[4,6]imidazo[1,2-a]pyridinyl, carbazolyl, cinnolinyl, dibenzofuranyl, furanyl, thienyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, 2,3-naphthyridinyl, pteridinyl, purinyl, pyrrolyl, pyrazolyl, pyridinyl, pyrazinyl, pyrimidinyl, pyridazinyl, quinazolinyl, quinoxalinyl, quinolyl, quinuclidinyl, isoquinolyl, thiazolyl, thiadiazolyl, triazolyl, tetrazolyl, triazinyl and thiophenyl.

The term "$C_2$-$C_{12}$ heteroaryl" refers to an aromatic cyclic group having at least one heteroatom (e.g., 2, 3, 4, or 5 heteroatoms) selected from the group consisting of N, O, and S as a ring-forming atom in addition to 2 to 12 carbon atoms (e.g., 1, 2, 3, 3, 4, 4, 5, 6, 7, 8, 9, 10, 11, or 12 carbon atoms).

The term "carbocycle" refers to an aromatic or non-aromatic (partially or fully saturated) carbocycle, such as $C_{3-7}$ carbocycle, $C_{5-7}$ carbocycle, $C_{5-12}$ carbocycle, $C_{5-10}$ monocyclic carbocycle, and the like. Examples of carbocycle include cycloalkyl, cycloalkenyl, cycloalkynyl, and aryl, such as cyclopropane, cyclobutane, cyclopentane, cyclohexane, cycloheptane, cyclobutene, cyclopentene, cyclohexene, cycloheptene, cyclobutadiene, cyclopentadiene, cyclohexadiene, cycloheptadiene, or benzene ring.

The term "cyclic group" or "ring", such as a 3- to 12-membered cyclic group or a 3- to 12-membered ring, includes a $C_{3-12}$ carbocyclic ring, a 3- to 12-membered heterocyclic ring and a 6- to 12-membered aromatic ring or a 5- to 12-membered heteroaromatic ring. The carbocyclic, heterocyclic, aromatic and heteroaromatic rings herein have the same definitions as above, and examples thereof include: pyrroline, pyrrolidine, imidazoline, imidazolidine, triazolidine, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydroxepine, dihydrothiophene, tetrahydrothiophene, dihydrothiopyran, tetrahydrothiopyran, dihydrothiepine, tetrahydrothiepine, perhydrothiepine, dihydrozole, tetrahydrozole (azolidine), dihydroisozole, tetrahydroisozole (isazolidine), dihydrothiazole, tetrahydrothiazole (thiazolidine), dihydroisothiazole, tetrahydroisothiazole (isothiazolidine), dihydrofurazan, tetrahydrofurazan, dihydrodiazole, tetrahydrodiazole (diazolidine), dihydrozine, tetrahydrozine, dihydrodiazine, tetrahydrodiazine, dihvdrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, thiazine, dioxolane, dioxane, dithiolane, dithiane, pyrrole, imidazole, triazole, tetrazole, pyrazole, pyridine, piperazine, pyrimidine, pyridazine, azepine, diazepine, furan, pyran, oxane, thiophene, thiopyran, thiane, azole, isozole, thiazole, isothiazole, furazan, diazole, zine, diazine, thiadiazole, thiazine, thiadiazine, thiazepine, or thiodiazepine rings.

In the present specification,

means the connection position.

The term "optionally substituted amino" refers to —NH$_2$, mono- or di-substituted amino, and 5- to 7-membered cyclic amino, such as, an amino group optionally substituted with one or more substituents selected from C$_{1-6}$ alkyl (such as methyl).

The term "primary amine" refers to a compound formed by the substitution of one hydrogen in an ammonia molecule with a hydrocarbyl group R", wherein R" is optionally substituted alkyl, optionally substituted aryl, or optionally substituted heteroaryl as defined above. In some embodiments, R" is alkyl, haloalkyl, aryl, heteroaryl, alkylaryl, or alkylheteroaryl. In some embodiments, R" is C$_{1-6}$alkyl, C$_{1-6}$ haloalkyl, C$_{6-12}$ aryl, C$_2$-C$_{12}$ heteroaryl, C$_{1-6}$ alkyl C$_{6-12}$ aryl, or C$_{1-6}$ alkyl C$_2$-C$_{12}$ heteroaryl. In some embodiments, R" is alkyl or haloalkyl. In some embodiments, R" is C$_{1-6}$ alkyl.

The term "acyl" as used herein refers to a group having the structure —C(O)R", wherein R" is as defined above. The term "optionally substituted acyl" means that the R" moiety in this group is substituted or unsubstituted.

The term "sulfonyl" as used herein refers to a group having the structure —SO$_2$R", wherein R" is as defined above. The term "optionally substituted sulfonyl" means that the R" moiety in this group is substituted or unsubstituted.

The term "alkylamido" as used herein refers to a group having the formula —NHC(O)—Ri, wherein Ri is an alkyl group as defined above. For example, C$_{1-7}$ alkylamido refers to an alkylamido having 1 to 7 carbon atoms (excluding the carbon atom of the carbonyl). The term "optionally substituted alkylamido" means that the NH moiety and/or the alkyl moiety in the alkylamido is optionally substituted. Examples of optionally substituted alkylamido include, but are not limited to, —N(alkyl)C(O)-Ri.

The term "optionally substituted" means that the group is unsubstituted or substituted with one or more (e.g., 1 to 4, 1 to 3, or 1 to 2) substituents. When the group is substituted, the substituents are individually and independently selected from one or more of halo, hydroxy, alkyl, haloalkyl, hydroxyalkyl, alkenyl, alkynyl, cycloalkyl, aryl, heteroaryl, heterocyclyl, alkoxy, aryloxy, heteroaryloxy, mercapto, alkylthio, arylthio, cyano, carbonyl, thiocarbonyl, alkylamido, 0-carbamoyl, N-carbamoyl, O-thiocarbamoyl, N-thiocarbamoyl, C-amido, N-amido, S-sulfinamido, N-sulfinamido, carboxyl, C-carboxyl, O-carboxyl, isocyanato, cyanothio, isothiocyanato, nitro, ester group, silyl, trihalomethanesulfonyl, amino including mono- and di-substituted amino groups, protected derivatives thereof, and the like. These listed substituents may be further optionally substituted with alkyl or halo. Whenever a group is described as being "optionally substituted", the group may be substituted with one of the above substituents.

When a group is substituted with more than one substituent, the substituents may be the same or different, and any substituted functional group herein may be substituted at 1 to 4 different positions, and those 1 to 4 substituents may be each independently substituted at 1 to 4 positions.

It is known to those skilled in the art that the processes of the present disclosure may comprise, when necessary, steps for the protection and deprotection of certain groups, and that the commonly used protecting groups (e.g., protecting groups of hydroxy group, thiol group, and amino group), the principles for the selection of the protecting groups and the methods for deprotection are well known in the art.

The inventions of the present application provide the following advantages:

The present application can realize a one-pot preparation of intermediates of quinolones without the need to isolate the intermediates, and directly obtain structurally complex molecules, which is more economically favourable and environmentally friendly.

In addition, the processes of the present disclosure have the advantages of short reaction steps, good selectivity and high yield, and the yields of the quinolone drugs or intermediates thereof obtained by the processes of the present disclosure are not less than 55%, not less than 60%, not less than 70%, or not less than 80%, and sometimes even 90% or more. Moreover, raw materials are cheap and easily available.

EXAMPLES

Specific embodiments of the present disclosure are described in further detail below in conjunction with the examples. The following examples are used for illustrative purposes only and are not intended to limit the scope of the present application.

Example 1

Synthesis of Ciprofloxacin and Grepafloxacin Analogs

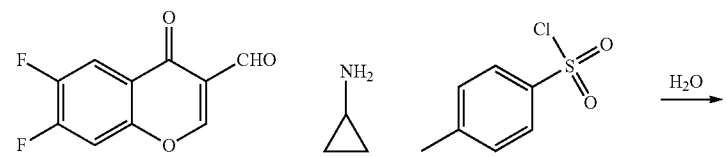

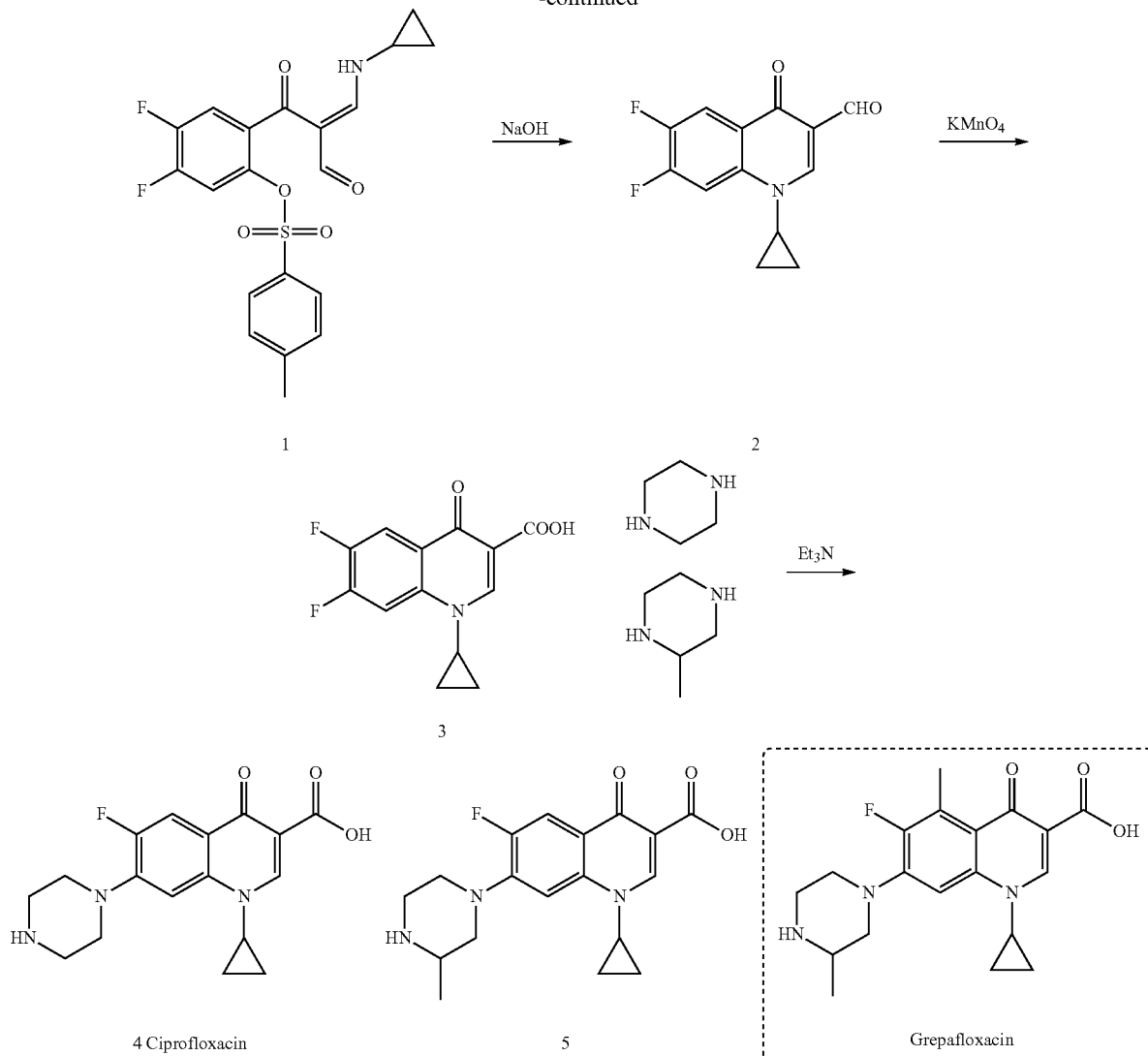

4 Ciprofloxacin

5

Grepafloxacin

The specific procedure for the synthesis of ciprofloxacin was as follows: 6,7-Difluoro-3-formylchromone (0.5 mmol), cyclopropylamine (1.2 mmol), p-toluenesulfonyl chloride (0.5 mmol) were firstly added in water (5.0 mL) in a 25 mL round bottom flask. After the reaction was performed at 100° C. for 5 h, the reaction was detected by thin layer chromatography. The reaction was completed when no 6,7-difluoro-3-formylchromone and p-toluenesulfonyl chloride remained. Then the reaction solution was cooled to room temperature, and extracted with ethyl acetate for three times (15.0 mL each time). The organic phase was dried over anhydrous sodium sulfate, and then separated by column chromatography to give the target compound 1 in a yield of 67%. $^1$H NMR (400 MHz, CDCl$_3$) δ 11.16-10.86 (m, 1H), 9.05 (d, J=1.5 Hz, 1H), 8.07 (s, 1H), 7.63 (dt, J=8.4, 1.7 Hz, 2H), 7.23 (ddd, J=9.8, 8.4, 1.5 Hz, 1H), 7.18-7.07 (m, 1H), 3.00 (ddq, J=32.7, 7.6, 3.7 Hz, 1H), 2.46 (s, 3H), 1.05-0.91 (m, 2H), 0.92-0.79 (m, 2H). $^{13}$C NMR (101 MHz, CDCl$_3$) δ 190.54, 189.16, 187.40, 186.74, 160.57, 151.98, 149.44, 147.71, 147.58, 146.22, 146.05, 141.48, 141.39, 131.78, 131.67, 130.42, 129.98, 129.94, 128.53, 118.34, 118.15, 117.95, 117.76, 113.43, 113.29, 113.23, 113.08, 110.39, 77.35, 77.24, 77.04, 76.72, 31.14, 30.99, 21.82, 21.81, 6.70, 6.61. HRMS (ESI) calcd for $C_{20}H_{18}F_2NO_5S$ [M+H]$^+$ 422.0868, found: 422.0871.

Compound 1 (0.2 mmol) was dissolved in dimethyl sulfoxide (DMSO), and then to the system was added sodium hydroxide (0.4 mmol). The reaction system was heated to 120° C. and reacted for 6 hours. The reaction was then detected by thin layer chromatography, and when no starting materials remained, the reaction solution was cooled to room temperature, and then extracted with ethyl acetate for three times (15 mL each time). The organic phase was dried over anhydrous sodium sulfate, and then separated by column chromatography to give the target compound 2 in a yield of 89%. $^1$H NMR (400 MHz, CDCl$_3$) δ 10.36 (s, 1H), 8.43 (s, 1H), 8.27 (dd, J=10.1, 8.6 Hz, 1H), 7.80 (dd, J=11.2, 6.3 Hz, 1H), 3.49 (t, J=3.7 Hz, 1H), 1.40 (d, J=6.8 Hz, 2H), 1.25-1.14 (in, 2H). $^{13}$C NMR (101 MHz, CDCl$_3$) δ 188.94, 175.36, 154.95, 154.81, 152.40, 152.25, 150.25, 150.12, 147.74, 147.60, 145.93, 138.16, 138.06, 126.17, 126.12, 126.09, 116.79, 115.09, 115.07, 114.91, 114.88, 106.35, 106.13, 99.98, 77.35, 77.24, 77.04, 76.86, 76.72, 76.54, 35.12, 8.24. HRMS (ESI) calcd for $C_{13}H_{10}F_2NO_2$[M+H]$^+$ 250.0674, found: 250.0679.

Compound 2 (0.2 mmol) was dissolved in a mixture of 1,4-dioxane and $H_2O$ (3 mL, 2:1), and sodium hydroxide and potassium permanganate (0.4 mmol each) were weighed and added into the reaction solution. The reaction was stirred at room temperature for 7 hours, and then detected by thin layer chromatography. When no starting materials remained, the solvents were evaporated to dryness, and then the residue was separated by column chromatography to give the target compound 3 in a yield of 57%. The compound 3 (0.2 mmol), piperazine (0.22 mmol) and triethylamine (0.22 mmol) were dissolved in 5 mL DMSO. The reaction system was heated to 150° C. under microwave conditions, stirred for 0.5 h, and then detected by thin layer chromatography. When no starting materials remained, the reaction solution was cooled to room temperature. The reaction solution was finally recrystallized in methanol to obtain ciprofloxacin 4 in a yield of 63%. $^1H$ NMR (400 MHz, $D_2O$) δ 8.29 (s, 1H), 7.23 (d, J=7.1 Hz, 1H), 7.02 (d, J=12.9 Hz, 1H), 3.42 (d, J=33.8 Hz, 8H), 1.28 (d, J=6.5 Hz, 2H), 1.00 (s, 2H). $^3C$ NMR (101 MHz, $D_2O$) δ 175.28, 168.41, 154.31, 151.81, 147.84, 144.50, 144.40, 138.62, 118.20, 118.12, 110.39, 110.16, 106.25, 105.24, 46.18, 46.13, 43.09, 36.02, 7.40. HRMS (ESI) calcd for $C_{17}H_{19}FN_3O_3[M+H]^+$ 322.1405, found: 322.1410.

In addition, the grepafloxacin analog 5 (yield: 72%) was isolated and obtained under the same conditions except that the piperazine was replaced with 2-methylpiperazine in this step. $^1H$ NMR (400 MHz, DMSO-$d_6$) δ 8.64 (s, 1H), 7.87 (d, J=13.3 Hz, 1H), 7.53 (d, J=7.4 Hz, 1H), 3.90-3.79 (m, 1H), 3.58 (s, 2H), 3.36 (s, 2H), 3.08 (s, 2H), 2.98 (d, J=8.7 Hz, 2H), 2.69 (s, 1H), 1.31 (d, J=6.8 Hz, 2H), 1.22-1.15 (m, 2H), 1.11 (d, J=6.3 Hz, 3H). $^3C$ NMR (101 MHz, DMSO) δ 176.76, 176.73, 166.39, 154.62, 152.15, 148.37, 145.65, 145.55, 139.65, 118.94, 118.86, 111.51, 111.28, 107.14, 106.72, 106.68, 56.22, 50.48, 49.43, 44.90, 36.32, 18.85, 8.04, 8.01. HRMS (ESI) calcd for $C_{18}H_{20}FN_3O_3[M+H]^+$ 346.1562, found: 346.1569.

Example 2

Synthesis of Norfloxacin and Pefloxacin

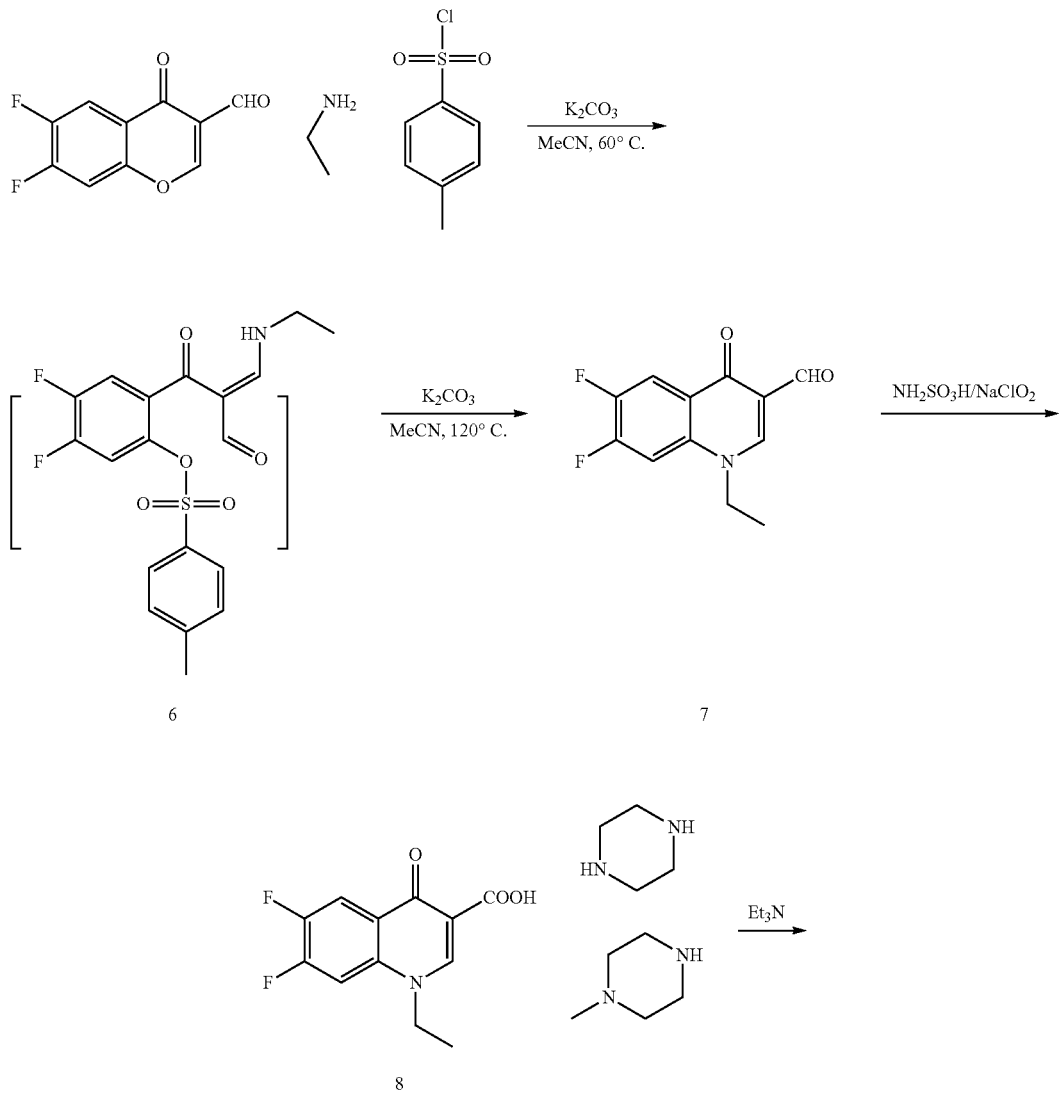

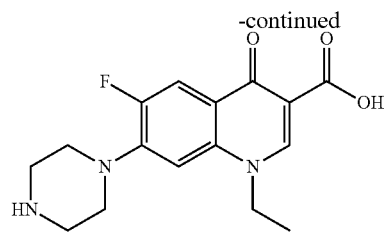

9 Norfloxacin

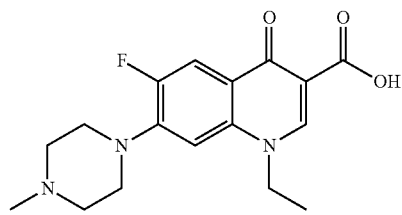

10 Pefloxacin

The specific procedure for the synthesis of norfloxacin was as follows:

To acetonitrile (5.0 mL) in a 25 mL round bottom flask were firstly added 6,7-difluoro-3-formylchromone (0.5 mmol), ethylamine (0.5 mmol), and p-toluenesulfonyl chloride (0.5 mmol), and then to the reaction system was added potassium carbonate (0.6 mmol). After the addition was completed, the reaction system was heated to 60° C., and reacted for 5 hours, and then detected by thin layer chromatography. When no 6,7-difluoro-3-phenylchromone remained, the reaction was completed (Intermediate 6 did not need to be isolated in this step). Potassium carbonate (0.6 mmol) was additionally added to the reaction system, and then the reaction system was heated to 120° C. and reacted for 8 hours. The reaction was monitored by thin layer chromatography. After completion of the reaction, the reaction solution was cooled to room temperature, and then extracted with ethyl acetate for three times (15 mL each time). The organic phase was dried over anhydrous sodium sulfate, and then separated by column chromatography to give the target compound 7 in a yield of 55%. $^1$H NMR (400 MHz, DMSO-$d_6$) δ 10.14 (s, 1H), 8.64 (s, 1H), 8.21-8.02 (m, 2H), 4.43 (q, J=7.1 Hz, 2H), 1.37 (t, J=7.1 Hz, 3H). $^{13}$C NMR (101 MHz, DMSO-$d_6$) δ 188.46, 174.58, 148.16, 137.02, 136.92, 126.74, 116.53, 114.05, 113.88, 108.23, 108.01, 49.25, 14.77. HRMS (ESI) calcd for $C_{12}H_{10}F_2NO_2$ [M+H]$^+$ 238.0647, found: 238.0652.

Compound 7 (0.2 mmol) was dissolved in water/DCM (3.0 mL, 1:2), and sulfamic acid/sodium chlorite (0.8 mmol each) were weighed and added into the reaction solution. The reaction was stirred at room temperature for 7 hours, and then detected by thin layer chromatography. When no starting materials remained, the solvents were evaporated to dryness, and then the residue was separated by column chromatography to give the target compound 8 in a yield of 57%. $^1$H NMR (400 MHz, DMSO-$d_6$) δ 14.87 (s, 1H), 9.09 (s, 1H), 8.43-8.20 (m, 2H), 4.58 (q, J=6.9 Hz, 2H), 1.39 (dd, J=13.0, 6.1 Hz, 3H). $^{13}$C NMR (101 MHz, DMSO-$d_6$) δ 176.91, 166.06, 156.00, 150.29, 137.36, 113.96, 108.45, 108.3, 108.22, 50.04, 14.98. HRMS (ESI) calcd for $C_{12}H_{10}F_2NO_2$[M+H]$^+$ 238.0647, found: 238.0652.

Compound 8 (0.2 mmol), piperazine (0.22 mmol) and triethylamine (0.22 mmol) were dissolved in 5 mL DMSO. The reaction system was heated to 150° C. under microwave conditions, stirred for 0.5 h, and then detected by thin layer chromatography. When no starting materials remained, the reaction solution was cooled to room temperature. The reaction solution was finally recrystallized in methanol to obtain norfloxacin 9 in a yield of 59%. $^1$H NMR (400 MHz, DMSO-$d_6$) δ 8.93 (s, 1H), 7.84 (d, J=13.5 Hz, 1H), 7.12 (d, J=7.3 Hz, 1H), 4.58 (q, J=7.0 Hz, 2H), 3.32-3.12 (m, 4H), 3.00-2.69 (m, 4H), 1.42 (t, J=7.1 Hz, 3H). $^{13}$C NMR (101 MHz, DMSO-$d_6$) δ 176.54, 176.52, 166.61, 154.58, 152.10, 148.82, 146.53, 146.43, 137.66, 119.43, 119.36, 111.62, 111.40, 107.48, 105.93, 105.90, 51.29, 51.25, 49.47, 45.87, 14.79. HRMS (ESI) calcd for $C_{16}H_{19}FN_3O_3$[M+H]$^+$ 254.0632, found: 320.1405.

In addition, pefloxacin 10 (yield: 66%) was isolated and obtained under the same conditions except that the piperazine was replaced with 2-methylpiperazine in the last reaction step. $^1$H NMR (400 MHz, DMSO-$d_6$) δ 15.37 (s, 1H), 8.95 (s, 1H), 7.90 (d, J=13.4 Hz, 1H), 7.17 (d, J=7.2 Hz, 1H), 4.59 (q, J=6.9 Hz, 2H), 2.53 (s, 2H), 2.26 (s, 2H), 1.42 (t, J=7.0 Hz, 3H). $^{13}$C NMR (101 MHz, DMSO-$d_6$) δ 176.62, 166.61, 154.28, 152.05, 148.98, 145.89, 137.67, 119.65, 111.73, 111.50, 107.51, 106.28, 54.76, 49.76, 49.51, 46.16, 14.84. HRMS (ESI) m/z calcd for $C_{17}H_{21}FN_3O_3{}^+$ (M+H)$^+$ 334.1561, found: 334.1563.

Example 3

Synthesis of Ivacaftor

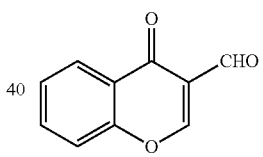

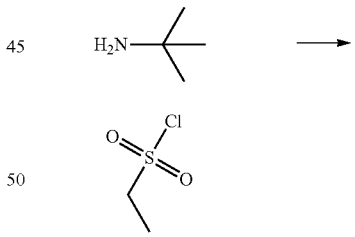

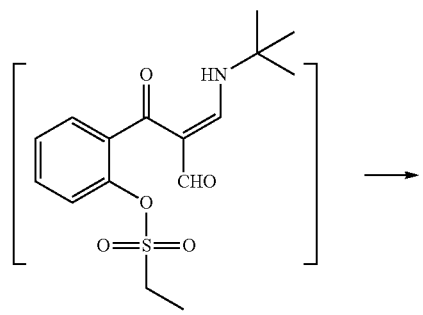

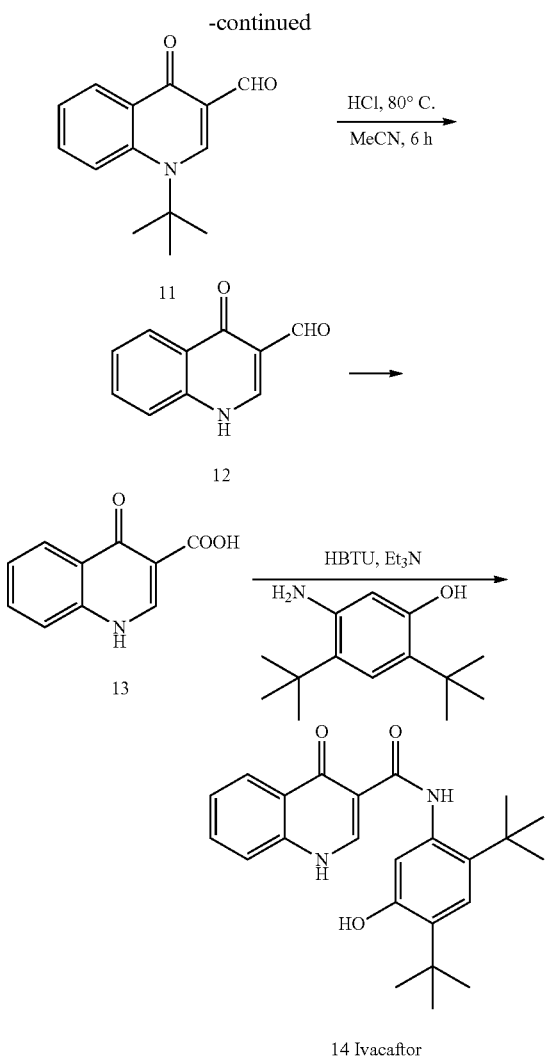

The specific procedure for the synthesis of ivacaftor was as follows:

The key intermediate 11 (yield: 71%) was directly synthesized using the one-pot process in Example 2. $^1$H NMR (400 MHz, CDCl$_3$) δ 10.37 (s, 1H), 8.66 (s, 1H), 8.56 (d, J=7.9 Hz, 1H), 7.92 (d, J=8.8 Hz, 1H), 7.64 (t, J=7.7 Hz, 1H), 7.42 (t, J=7.5 Hz, 1H), 1.84 (s, 9H). $^3$C NMR (101 MHz, CDCl$_3$) δ 188.66, 175.52, 142.13, 138.40, 130.65, 129.94, 126.95, 124.28, 119.37, 115.09, 62.73, 29.83. HRMS (ESI) m/z calcd for C$_{14}$H$_{16}$NO$_2$$^+$ (M+H)$^+$ 230.1176, found: 230.1177.

Compound 11 (0.2 mmol) was dissolved in a solution of 50% HCl/acetonitrile (5.0 mL), and stirred at 80° C. for 6 hours, and then the reaction was detected by thin layer chromatography. When no starting materials remained, the solvent was evaporated to dryness, and then the residue was isolated by column chromatography to give product 12 in a yield of 62%. Oxidation of the aldehyde group to carboxyl group under the oxidation conditions of Example 2 gave the target compound 13 in a yield of 66%. $^1$H NMR (400 MHz, DMSO-d$_6$) δ 15.36 (s, 1H), 13.51 (s, 1H), 8.90 (s, 1H), 8.30 (dd, J=8.2, 1.5 Hz, 1H), 7.89 (dd, J=6.8, 1.6 Hz, 1H), 7.88-7.78 (m, 1H), 7.61 (td, J=7.4, 6.6, 1.3 Hz, 1H). $^{13}$C NMR (101 MHz, DMSO-d$_6$) δ 178.79, 166.85, 145.62, 139.90, 134.41, 126.68, 125.51, 124.85, 120.13, 108.02, 40.64, 40.59, 40.43, 40.38, 40.17, 39.96, 39.75, 39.64, 39.54, 39.33. HRMS (ESI) m/z calcd for C$_{14}$H$_{15}$NO$_2$$^+$ (M+H)$^+$ 190.0499, found: 190.0501.

Compound 13 (0.2 mmol), O-benzotriazole-tetramethyl-uronium hexafluorophosphate (HBTU, 0.24 mmol), triethylamine (0.6 mmol) were weighed and dissolved in 3.0 mL DMF, and then to the reaction system was added 2-amino-3,5-di-tert-butylphenol (0.2 mmol). The reaction was carried out at room temperature for 6 h, and then detected by thin layer chromatography. When no starting materials remained, the solvent was evaporated to dryness and then the residue was separated by column chromatography to give ivacaftor 14 in a yield of 89%. $^1$H NMR (400 MHz, DMSO-d$_6$) δ 12.89 (s, 1H), 11.82 (s, 1H), 9.21 (s, 1H), 8.87 (s, 1H), 8.33 (d, J=8.1 Hz, 1H), 7.85-7.79 (m, 1H), 7.76 (d, J=8.2 Hz, 1H), 7.52 (t, J=7.5 Hz, 1H), 7.17 (s, 1H), 7.10 (s, 1H), 1.38 (s, 9H), 1.36 (s, 9H). $^{13}$C NMR (101 MHz, DMSO-d$_6$) δ 176.85, 163.27, 153.73, 144.63, 139.61, 133.98, 133.39, 132.73, 131.96, 126.45, 126.03, 125.61, 124.22, 119.58, 116.40, 111.34, 49.06, 34.80, 34.44, 31.03, 29.88. HRMS (ESI) calcd for C$_{24}$H$_{28}$N$_2$O$_3$[M+H]$^+$ 393.2173, found: 393.2171.

Example 4

Synthesis of a Precursor of Ozenoxacin

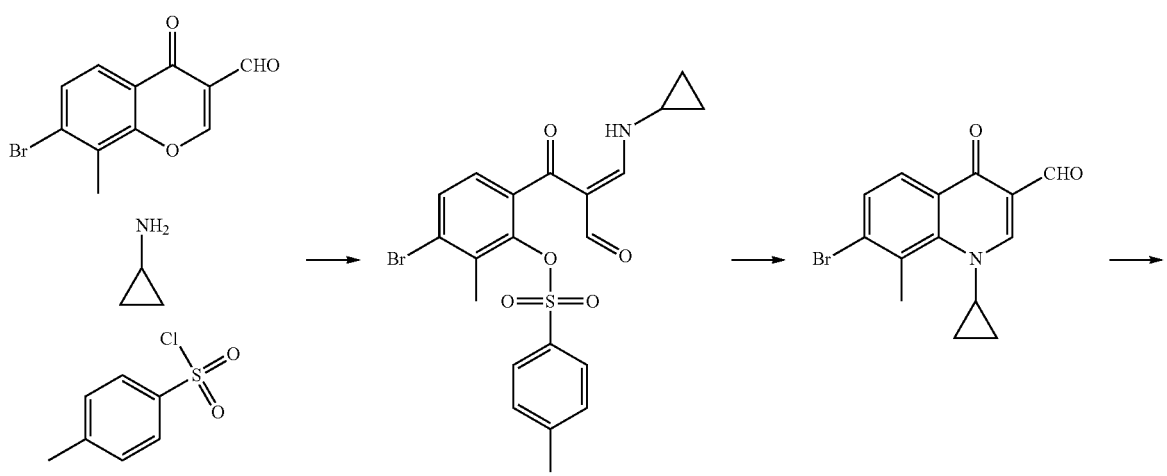

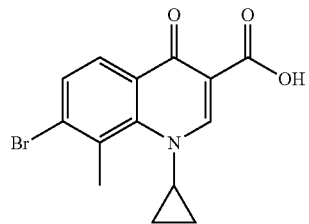

15

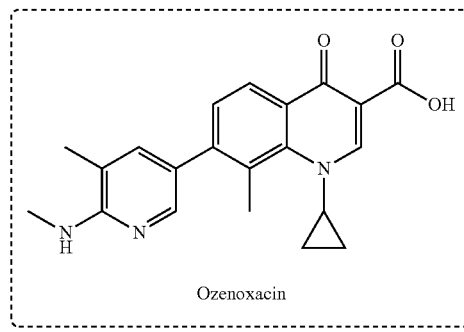

Ozenoxacin

The specific procedure for the synthesis of the precursor of ozenoxacin was as follows:

Precursor compound 15 of ozenoxacin can be rapidly constructed in a yield of 73% with reference to the synthetic method of the compound 3 in Example 1. $^1$H NMR (400 MHz, DMSO-$d_6$) δ 14.69 (s, 1H), 8.87 (s, 1H), 8.06 (d, J=8.6 Hz, 1H), 7.85 (d, J=8.6 Hz, 1H), 4.49-4.31 (m, 1H), 2.92 (s, 3H), 1.22 (d, J=6.3 Hz, 2H), 0.93 (s, 2H). $^{13}$C NMR (101 MHz, DMSO-$d_6$)$^{13}$C NMR (101 MHz, DMSO) δ 178.16, 165.79, 153.50, 143.18, 133.92, 131.06, 129.11, 126.60, 125.11, 108.50, 55.58, 42.10, 23.05, 10.82. HRMS (ESI) m/z calcd for $C_{14}H_{14}BrNO_3^+$ (M+H)$^+$ 322.0073, found: 322.0076.

Example 5

Synthesis of Oxolinic Acid

16 Oxolinic acid

The specific procedure for the synthesis of oxolinic acid was as follows:

Oxolinic acid 16 (yield: 69%) was finally isolated and obtained with reference to the synthetic method of the compound 3 in Example 1. $^1$H NMR (400 MHz, DMSO-$d_6$) δ 15.70 (s, 1H), 8.90 (s, 1H), 7.62 (d, J=11.1 Hz, 2H), 6.30 (s, 2H), 4.54 (q, J=7.0 Hz, 2H), 1.38 (t, J=7.1 Hz, 3H). $^{13}$C NMR (101 MHz, DMSO-$d_6$) δ 176.46, 166.79, 154.20, 147.57, 137.42, 121.88, 107.81, 103.74, 102.33, 97.71, 50.04, 15.09. HRMS (ESI) m/z calcd for $C_{13}H_{12}NO_5^+$ (M+H)$^+$ 262.0710, found: 262.0719.

Example 6

Synthesis of N-ethylquinolinone 19 from N-tert-butylquinolinone 17

-continued

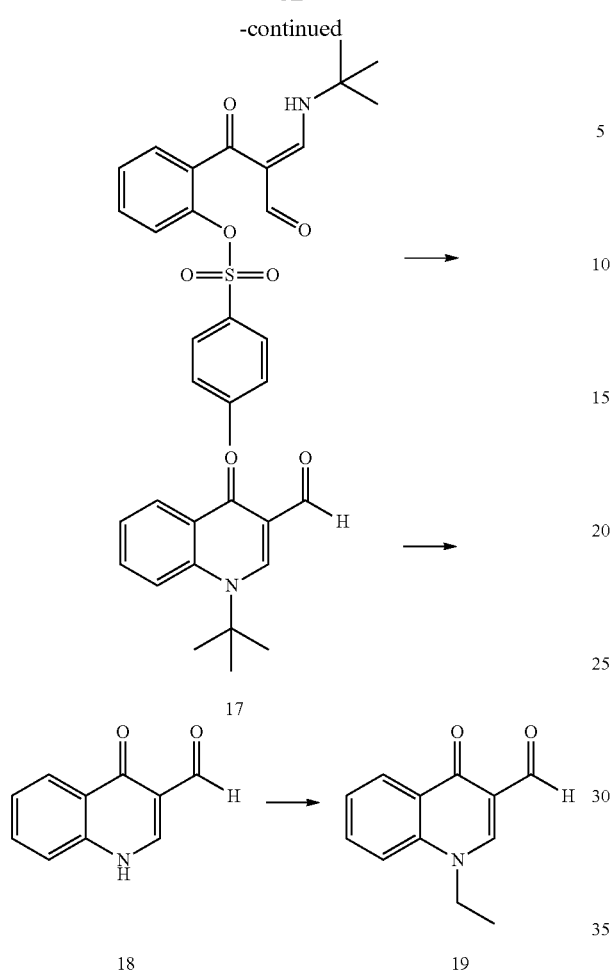

17

18   19

The specific procedure for the synthesis of N-ethylquinolinone 19 was as follows:

Compound 17 (yield: 71%) was synthesized with reference to the synthetic method of the compound 7 in Example 2. $^1$H NMR (400 MHz, CDCl$_3$) δ 10.37 (s, 1H), 8.66 (s, 1H), 8.56 (d, J=7.9 Hz, 1H), 7.92 (d, J=8.8 Hz, 1H), 7.64 (t, J=7.7 Hz, 1H), 7.42 (t, J=7.5 Hz, 1H), 1.84 (s, 9H). $^{13}$C NMR (101 MHz, CDCl$_3$) δ 188.66, 175.52, 142.13, 138.40, 130.65, 129.94, 126.95, 124.28, 119.37, 115.09, 62.73, 29.83. HRMS (ESI) m/z calcd for C$_{14}$H$_{16}$NO$_2^+$ (M+H)$^+$ 230.1176, found: 230.1177.

Compound 17 (0.2 mmol) was dissolved in a solution of 50% HCl/MeCN (5.0 mL), and the reaction system was heated to 80° C., and performed for 6 hours, and then detected by thin layer chromatography. When no starting materials remained, the solvent was evaporated to dryness to give crude product 18. To the reaction system were added potassium carbonate (0.6 mmol), iodoethane (0.22 mmol), and DMF (3.0 mL), and then the reaction system was reacted at 100° C. for 3 hours. The reaction was then detected by thin layer chromatography. When no starting materials remained, the solvent was evaporated to dryness, and then the residue was separated by column chromatography to give compound 19 in a yield of 92%. $^1$H NMR (400 MHz, CDCl$_3$) δ 10.43 (s, 1H), 8.56 (dd, J=8.0, 1.6 Hz, 1H), 8.35 (s, 1H), 7.90-7.68 (m, 1H), 7.57-7.46 (m, 2H), 4.31 (q, J=7.2 Hz, 2H), 1.58 (t, J=7.2 Hz, 3H). $^{13}$C NMR (101 MHz, CDCl$_3$) δ 189.50, 176.96, 145.50, 139.12, 133.26, 129.70, 127.67, 125.72, 117.28, 116.12, 77.35, 77.23, 77.03, 76.78, 76.71, 54.75, 49.20, 14.56. HRMS (ESI) calcd for C$_{12}$H$_{12}$NO$_2$[M+H]$^+$ 202.0863, found: 202.0867.

While the present disclosure has been described in detail above with reference to the general description and specific embodiments, it will be apparent to those skilled in the art that some modifications and improvements can be made on the basis of the present disclosure. Accordingly, such modifications and improvements as made without departing from the spirit of the present disclosure fall within the protection scope claimed by the present application.

The invention claimed is:
1. A process for the preparation of a compound of Formula I, comprising the steps of:
reacting a compound of Formula A with R$^5$NH$_2$ and R$^6$Cl in the presence of a base to form the compound of Formula I,

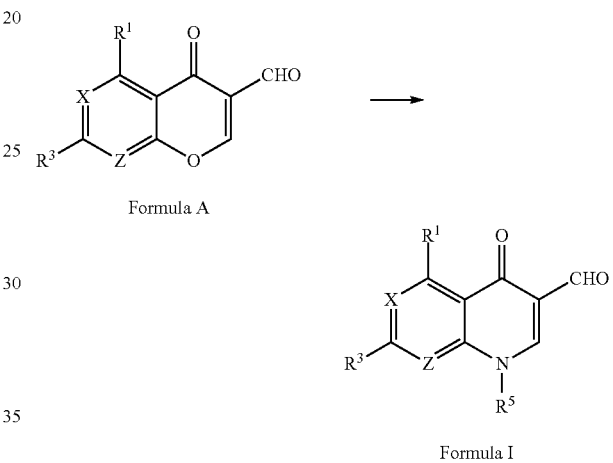

Formula A

Formula I wherein:
X is selected from the group consisting of CR$^2$ and N;
Z is selected from the group consisting of CR$^4$ and N;
R$^1$ is independently selected from the group consisting of hydrogen, alkyl, alkoxy, halo, NO$_2$, CN, optionally substituted amino, haloalkyl, aryl, and heteroaryl;
R$^2$ and R$^3$ are each independently selected from the group consisting of hydrogen, alkyl, alkoxy, halo, amino, NO$_2$, CN, haloalkyl, aryl, and heteroaryl; or R$^2$ and R$^3$ are linked together to form a ring;
R$^4$ is independently selected from the group consisting of hydrogen, alkyl, alkoxy, halo, amino, NO$_2$, CN, haloalkyl, aryl, and heteroaryl;
R$^5$ is independently selected from the group consisting of alkyl optionally substituted with OH or SH; cycloalkyl optionally substituted with halo; aryl; and heteroaryl; and
R$^6$ is independently selected from sulfonyl.
2. The process according to claim 1, wherein:
the base is selected from the group consisting of inorganic bases, organic bases, and combinations thereof; or
the base is selected from primary amines; or
the base is selected from the group consisting of potassium carbonate, cesium carbonate, sodium carbonate, sodium hydroxide, lithium tert-butoxide, sodium methoxide, sodium bicarbonate, sodium hydride, triethylamine, diisopropylamine, 1,8-diazabicyclo[5.4.0]undec-7-ene, 1,4-diazabicyclo[2.2.2]octane, and combinations thereof; or the base is selected from the group consisting of potassium carbonate, cesium carbonate, sodium carbonate, and combinations thereof; or the reaction is carried out in a solvent; or the reaction is carried out in a solvent selected from the group consisting of methanol, ethanol, acetonitrile, toluene, water, N,N-dimethylformamide, xylene, nitrobenzene, trifluorotoluene, N-methylpyrrolidone, 1,2-dichloroethane, 1,4-dioxane, and combinations thereof, or the reaction is carried out in a solvent selected from the group consisting of N,N-dimethylformamide, N-methylpyrrolidone, and a combination thereof; or the reaction is carried out at a temperature of 80° C.-200° C. or 100° C.-150° C.

3. A process for the preparation of a compound of Formula I, comprising the steps of:
i) reacting a compound of Formula A with $R^5NH_2$ and $R^6Cl$ in the presence of a base to form a compound of Formula B, and
ii) reacting the compound of Formula B in the presence of a base to form the compound of Formula I,
wherein the reaction of step ii) is carried out at a temperature higher than the reaction temperature of step i);

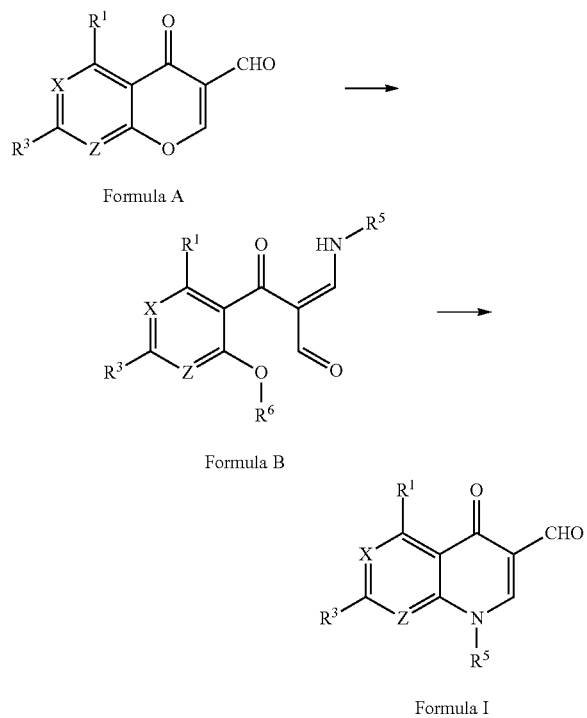

wherein:
X is selected from the group consisting of $CR^2$ and N;
Z is selected from the group consisting of $CR^4$ and N;
$R^1$ is independently selected from the group consisting of hydrogen, alkyl, alkoxy, halo, $NO_2$, CN, optionally substituted amino, haloalkyl, aryl, and heteroaryl;
$R^2$ and $R^3$ are each independently selected from the group consisting of hydrogen, alkyl, alkoxy, halo, amino, $NO_2$, CN, haloalkyl, aryl, and heteroaryl; or $R^2$ and $R^3$ are linked together to form a ring;
$R^4$ is independently selected from the group consisting of hydrogen, alkyl, alkoxy, halo, amino, $NO_2$, CN, haloalkyl, aryl, and heteroaryl;

$R^5$ is independently selected from the group consisting of alkyl optionally substituted with OH or SH; cycloalkyl optionally substituted with halo; aryl; and heteroaryl; and $R^6$ is independently selected from sulfonyl.

4. The process according to claim 3, wherein:
the base in step i) is selected from the group consisting of inorganic bases, organic bases, and combinations thereof; or
the base in step i) is selected from primary amines, preferably excess primary amines; or
the base in step i) is selected from the group consisting of potassium carbonate, cesium carbonate, sodium carbonate, sodium hydroxide, lithium tert-butoxide, sodium methoxide, sodium bicarbonate, sodium hydride, triethylamine, diisopropylamine, 1,8-diazabicyclo[5.4.0]undec-7-ene, 1,4-diazabicyclo[2.2.2]octane, and combinations thereof; or
the base in step i) is selected from the group consisting of lithium tert-butoxide, potassium carbonate, cesium carbonate, sodium carbonate, sodium bicarbonate, triethylamine, diisopropylamine, 1,8-diazabicyclo[5.4.0]undec-7-ene, and combinations thereof; or
the reaction of step i) is carried out in a first solvent; or
the reaction of step i) is carried out in a first solvent selected from the group consisting of methanol, ethanol, acetonitrile, toluene, water, dimethyl sulfoxide, N,N-dimethylformamide, 1,4-dioxane, and combinations thereof; or
the reaction of step i) is carried out at a temperature ranging from room temperature to 150° C., or from room temperature to 100° C.

5. The process according to claim 3, wherein:
the base in step ii) is selected from inorganic bases; or
the base in step ii) is selected from the group consisting of potassium carbonate, cesium carbonate, sodium carbonate, sodium hydroxide, lithium tert-butoxide, sodium methoxide, sodium bicarbonate, sodium hydride, and combinations thereof, or the base in step ii) is selected from the group consisting of potassium carbonate, cesium carbonate, sodium carbonate, and combinations thereof; or
the reaction of step ii) is carried out in a second solvent; or
the reaction of step ii) is carried out in a second solvent selected from the group consisting of xylene, nitrobenzene, trifluorotoluene, 1,2-dichloroethane, acetonitrile, toluene, dimethylsulfoxide, N,N-dimethylformamide, 1,4-dioxane, N-methylpyrrolidone, and combinations thereof; or
the reaction of step ii) is carried out in a second solvent selected from the group consisting of N-methylpyrrolidone, N,N-dimethylformamide, and a combination thereof; or
the reaction of step ii) is carried out at a temperature of 100° C.-200° C., or 100° C.-150° C.

6. The process according to claim 1, wherein:
$R^1$ is independently selected from the group consisting of hydrogen, $C_{1-6}$ alkyl, $C_{1-6}$ alkoxy, halo, $NO_2$, CN, optionally substituted amino, $C_{1-6}$ haloalkyl, $C_{6-12}$ aryl, and $C_{2-12}$ heteroaryl; or
$R^1$ is independently selected from the group consisting of hydrogen, $C_{1-4}$ alkyl, $C_{1-4}$ alkoxy, halo, $NO_2$, CN, optionally substituted amino, $C_{1-4}$ haloalkyl, $C_{6-10}$ aryl, and $C_{2-10}$ heteroaryl; or R[1] is independently selected from the group consisting of hydrogen, methyl, methoxy, F, Cl, Br, I, NO$_2$, CN, CF$_3$, and amino; or R[1] is independently selected from the group consisting of hydrogen, alkyl, and amino; or R[1] is independently selected from the group consisting of hydrogen, methyl, and amino; or R[2] and R[3] are each independently selected from the group consisting of hydrogen, C$_{1-6}$ alkyl, C$_{1-6}$ alkoxy, halo, amino, NO$_2$, CN, C$_{1-6}$ haloalkyl, C$_{6-12}$ aryl, and C$_{2-12}$ heteroaryl; or R[2] and R[3] are linked together to form a 3- to 12-membered ring, e.g., a 5- to 12-membered non-aromatic heterocycle; or R[2] and R[3] are each independently selected from the group consisting of hydrogen, C$_{1-4}$ alkyl, C$_{1-4}$ alkoxy, halo, amino, NO$_2$, CN, C$_{1-4}$ haloalkyl, C$_{6-10}$ aryl, and C$_{2-10}$ heteroaryl; or R[2] and R[3] are linked together to form a 5- to 10-membered ring, e.g., a 5- to 10-membered non-aromatic heterocycle; or R[2] and R[3] are each independently selected from the group consisting of hydrogen, methyl, methoxy, F, Cl, Br, I, amino, NO$_2$, CN, and CF$_3$; or R[2] and R[3] are each independently selected from the group consisting of hydrogen, halo, and amino; or R[2] and R[3] are each independently selected from the group consisting of hydrogen, and halo; or R[2] and R[3] form a 5- to 7-membered non-aromatic heterocycle, such as 1,3-dioxole; or R[4] is independently selected from the group consisting of hydrogen, C$_{1-6}$ alkyl, C$_{1-6}$ alkoxy, halo, amino, NO$_2$, CN, C$_{1-6}$ haloalkyl, C$_{6-12}$ aryl, and C$_{2-12}$ heteroaryl; or R[4] is independently selected from the group consisting of hydrogen, C$_{1-4}$ alkyl, C$_{1-4}$ alkoxy, halo, amino, NO$_2$, CN, C$_{1-4}$ haloalkyl, C$_{6-10}$ aryl, and C$_{2-10}$ heteroaryl; or R[4] is independently selected from the group consisting of hydrogen, methyl, methoxy, F, Cl, Br, I, NH$_2$, NO$_2$, CN, and CF$_3$; or R[4] is independently selected from the group consisting of hydrogen, alkyl, alkoxy, halo, NH$_2$, and CN; or R[4] is independently selected from the group consisting of hydrogen, methyl, methoxy, F, C$_1$, NH$_2$, and CN; or R[5] is independently selected from the group consisting of hydrogen; C$_{1-6}$ alkyl optionally substituted with OH or SH; 3- to 12-membered cycloalkyl optionally substituted with halo; C$_{6-12}$ aryl; and C$_{2-12}$ heteroaryl; or R[5] is independently selected from the group consisting of C$_{1-6}$ alkyl optionally substituted with OH or SH; 3- to 12-membered cycloalkyl optionally substituted with halo; C$_{6-12}$ aryl; and C$_{2-12}$ heteroaryl; or R[5] is independently selected from hydrogen; C$_{1-4}$ alkyl optionally substituted with OH or SH; 3- to 8-membered cycloalkyl optionally substituted with halo; C$_{6-10}$ aryl; and C$_{2-10}$ heteroaryl; or R[5] is independently selected from the group consisting of hydrogen; alkyl optionally substituted with OH or SH; and cycloalkyl optionally substituted with halo; or R[5] is independently selected from the group consisting of alkyl optionally substituted with OH or SH; and cycloalkyl optionally substituted with halo; or R[5] is independently selected from the group consisting of hydrogen, ethyl, cyclopropyl, fluorocyclopropyl, tert-butyl, —(CH$_2$)$_2$OH, —(CH$_2$)$_2$SH, —CH(CH$_3$)CH$_2$OH, and —CH(CH$_3$)CH$_2$SH; or R[5] is independently selected from the group consisting of ethyl, cyclopropyl, fluorocyclopropyl, tert-butyl, —(CH$_2$)$_2$SH, and —CH(CH$_3$)CH$_2$OH; or R[6] is independently selected from the group consisting of p-toluenesulfonyl and ethylsulfonyl; or the halo is selected from the group consisting of F, Cl, Br, and I; or at least one of R[2] and R[3] is halo; or R[3] is halo; or the compound of Formula I is selected from the group consisting of:

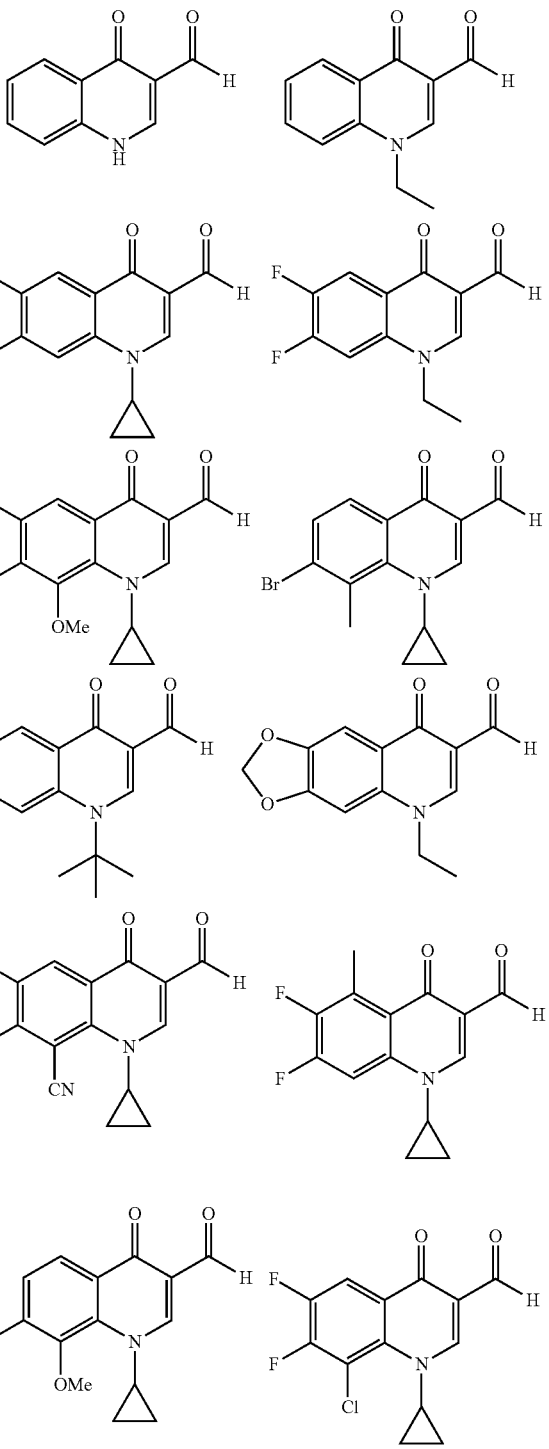

-continued

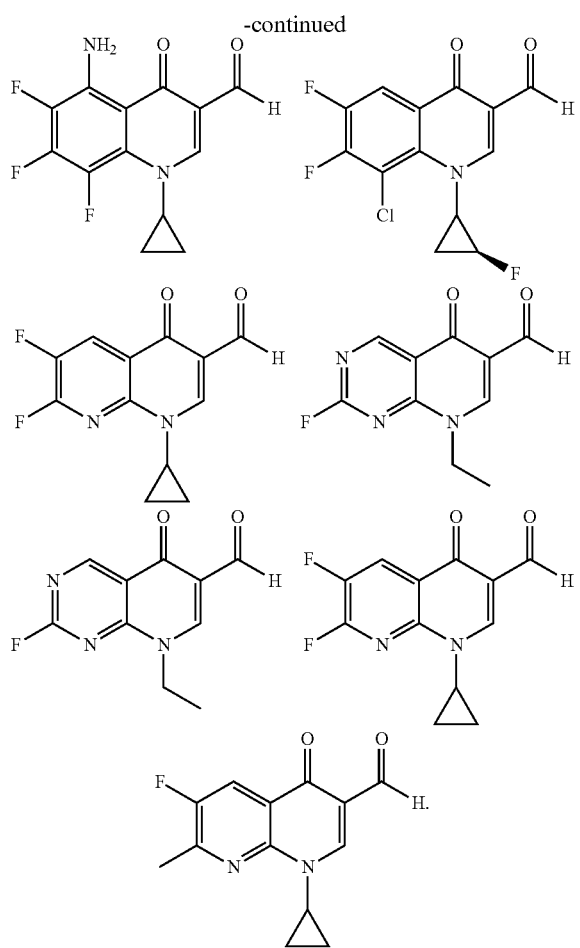

7. A process for the preparation of a compound of Formula II, comprising the steps of:
preparing a compound of Formula I according to the process of claim 1; and
oxidizing the compound of Formula I to generate the compound of Formula II,

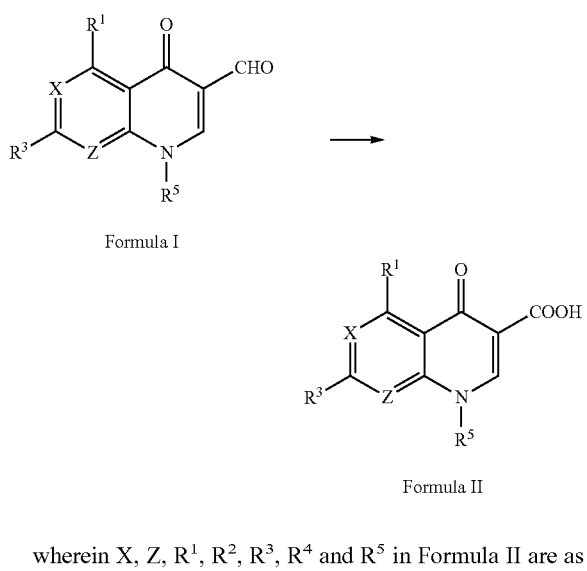

Formula I

Formula II wherein X, Z, $R^1$, $R^2$, $R^3$, $R^4$ and $R^5$ in Formula II are as defined in Formula I.

8. The process according to claim 7, wherein the compound of Formula II is selected from the group consisting of:

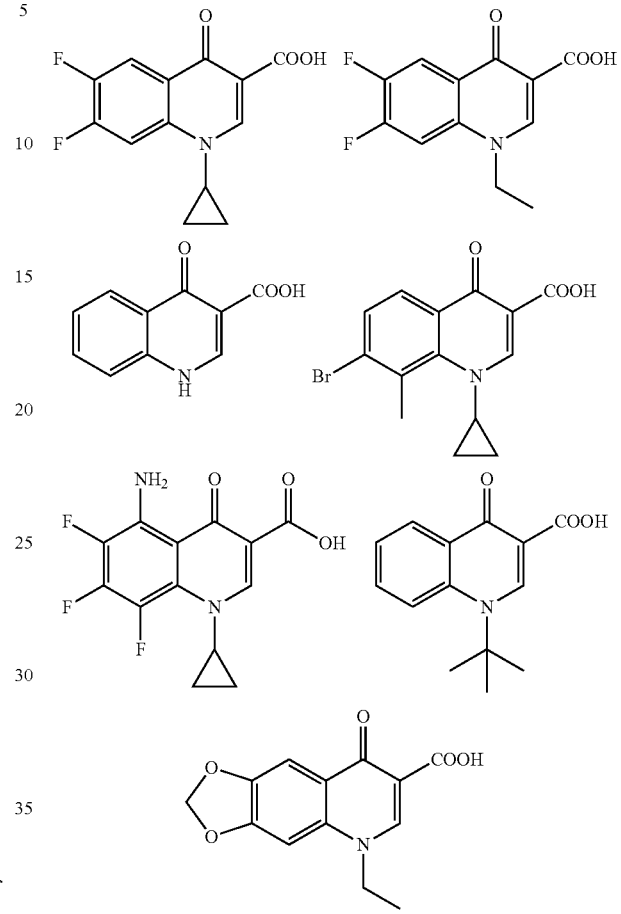

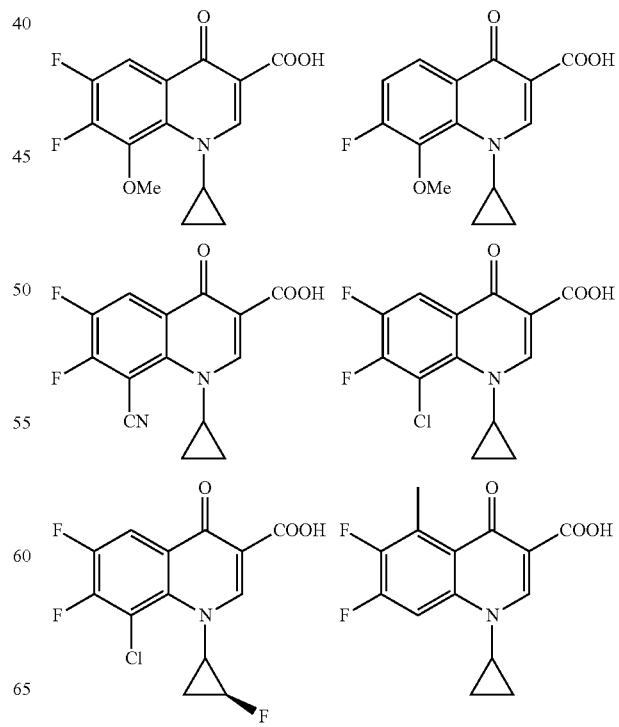

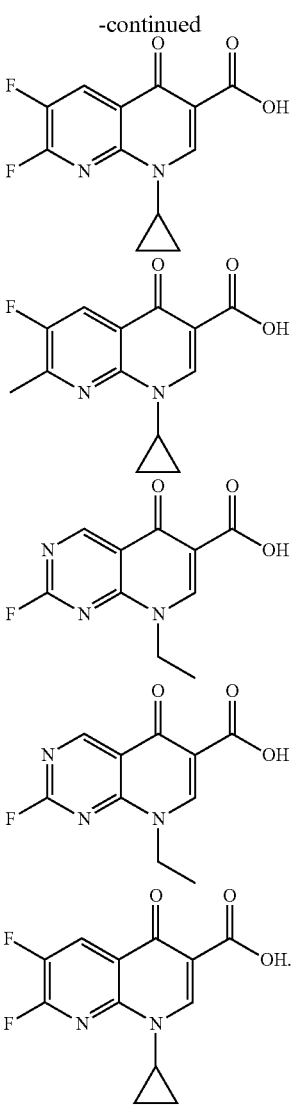

9. A process for the preparation of a compound of Formula III, comprising the steps of:
preparing a compound of Formula I according to the process of claim 1;
oxidizing the compound of Formula I to generate a compound of Formula II; and
reacting the compound of Formula II with an optionally substituted nitrogen-containing heterocyclic compound in the presence of a base to generate the compound of Formula III, or subjecting the compound of Formula II to a Stille coupling reaction to form the compound of Formula III,

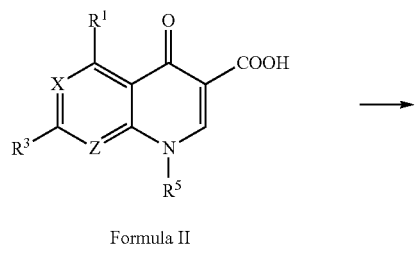

Formula II

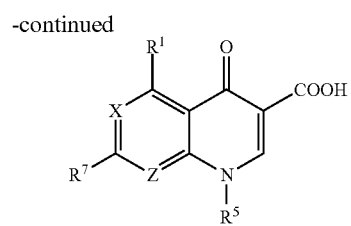

Formula III wherein:
in Formula II, $R^2$ and $R^3$ do not form a ring, and $R^3$ is halo; and
in Formula III, X, Z, $R^1$, $R^2$, $R^4$, and $R^5$ are as defined in Formula II, and $R^7$ is selected from the group consisting of optionally substituted N-heterocyclyl, optionally substituted heteroaryl, and optionally substituted aryl.

10. The process according to claim 9, wherein:
the optionally substituted nitrogen-containing heterocyclic compound is selected from nitrogen-containing heterocyclic compounds optionally substituted with one or more substituents selected from the group consisting of alkyl optionally substituted with $NH_2$; =N(alkoxy); alkoxy; cycloalkyl; hydroxy; and optionally substituted amino; or the optionally substituted nitrogen-containing heterocyclic compound is selected from the group consisting of piperidine, piperazine, tetrahydropyrrole, pyrrolomorpholine, pyrrolopiperidine, azaspiro[2.4]heptane, and azepane, each optionally substituted with one or more substituents selected from the group consisting of $C_{1-6}$ alkyl optionally substituted with $NH_2$; =N($C_{1-6}$ alkoxy); $C_{1-6}$ alkoxy; 3- to 7-membered cycloalkyl; hydroxy; and $NH_2$; wherein said $NH_2$ is optionally substituted with one or more groups selected from $C_{1-6}$ alkyl; or $R^7$ is selected from the group consisting of N-heterocyclyl, heteroaryl, and aryl, each optionally substituted with one or more substituents selected from the group consisting of alkyl optionally substituted with $NH_2$; =N(alkoxy); alkoxy; cycloalkyl; hydroxy; alkylamido optionally substituted with alkyl; and optionally substituted amino; or $R^7$ is selected from the group consisting of 5- to 12-membered N-heterocyclyl, $C_{2-12}$ heteroaryl, and $C_{6-12}$ aryl, each optionally substituted with one or more substituents selected from the group consisting of $C_{1-6}$ alkyl optionally substituted with $NH_2$; =N($C_{1-6}$ alkoxy); $C_{1-6}$ alkoxy; 3- to 7-membered cycloalkyl; hydroxy; $C_{1-6}$ alkylamido optionally substituted with $C_{1-6}$ alkyl; and $NH_2$ optionally substituted with one or more $C_{1-6}$ alkyl; or $R^7$ is selected from 5- to 12-membered N-heterocyclyl optionally substituted with one or more substituents selected from the group consisting of $C_{1-6}$ alkyl optionally substituted with $NH_2$; =N($C_{1-6}$ alkoxy); 3- to 7-membered cycloalkyl; hydroxy; and $NH_2$ optionally substituted with one or more $C_{1-6}$ alkyl; or $R^7$ is selected from $C_{2-12}$ heteroaryl optionally substituted with one or more substituents selected from the group consisting of $C_{1-6}$ alkyl; $C_{1-6}$ alkylamido optionally substituted with $C_{1-6}$ alkyl; and $NH_2$ optionally substituted with one or more $C_{1-6}$ alkyl; or the N-heterocyclyl is N-heterocycloalkyl; or $R^7$ is selected from the group consisting of:
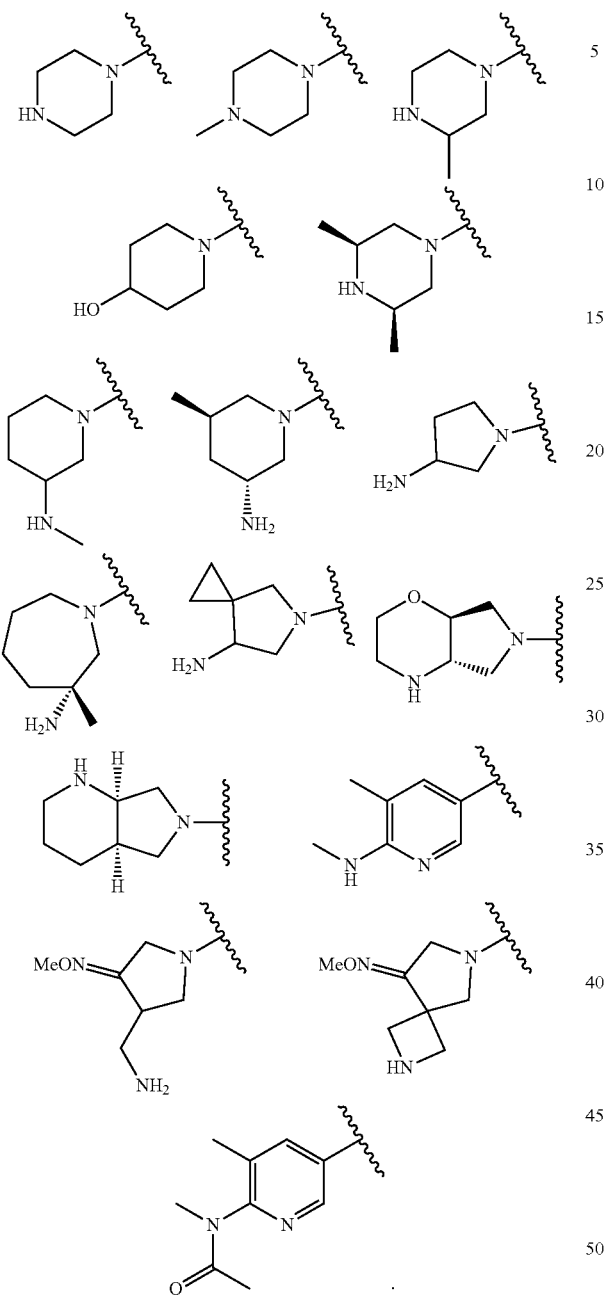
11. The process according to claim 9, wherein:
the compound of Formula III is selected from the group consisting of:
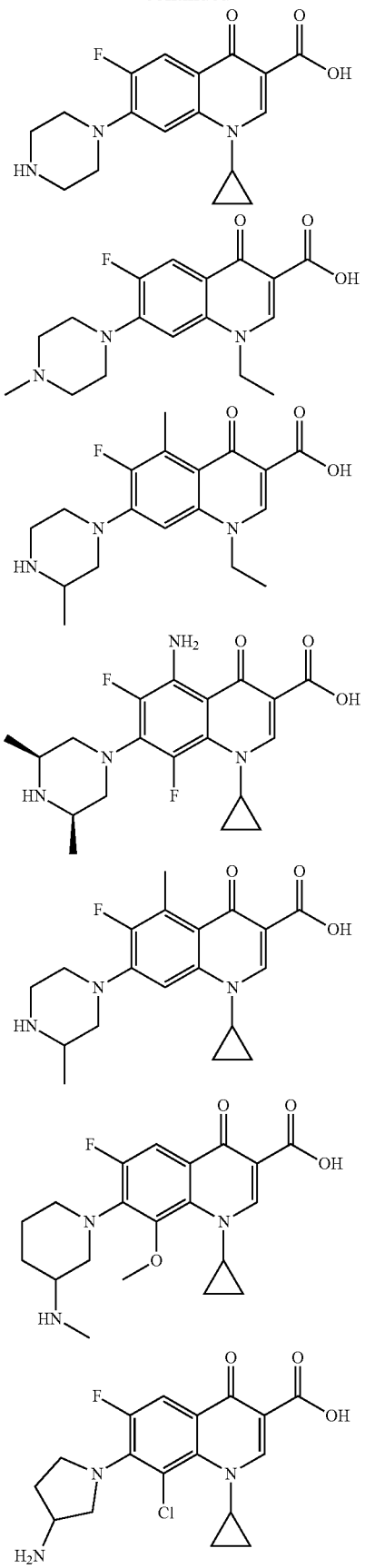

-continued
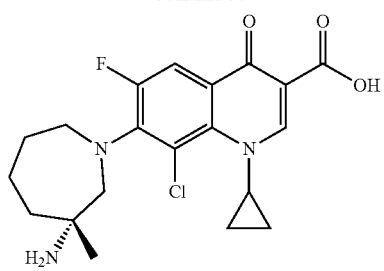
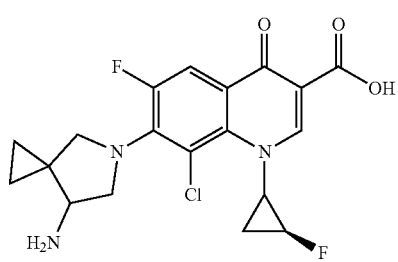
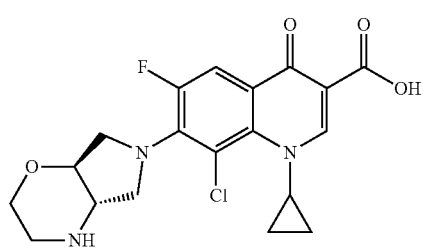
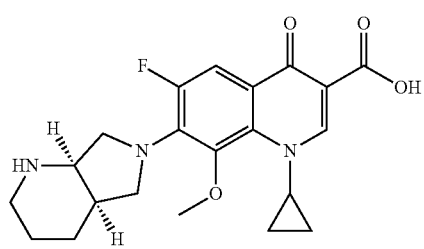
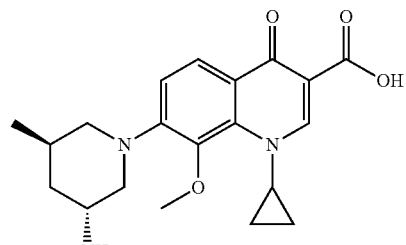
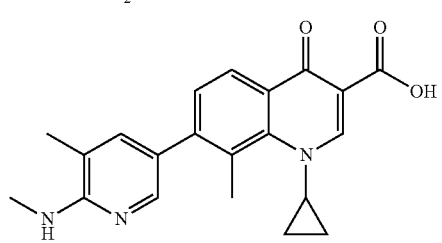
-continued
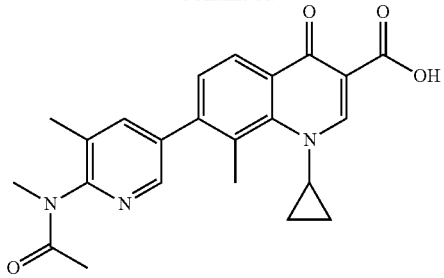
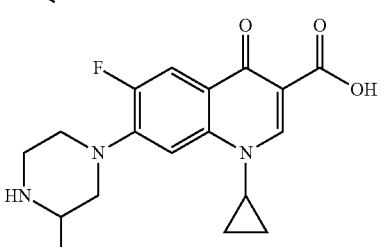
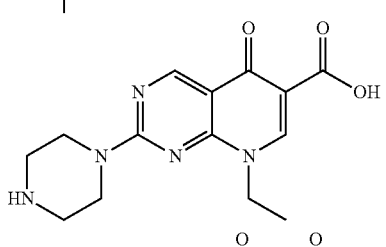
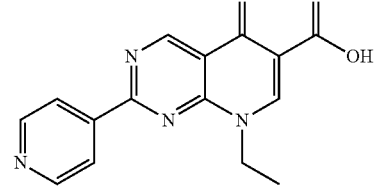
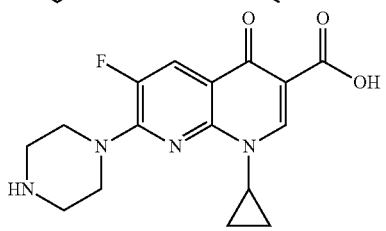
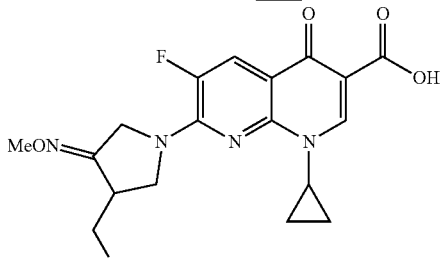
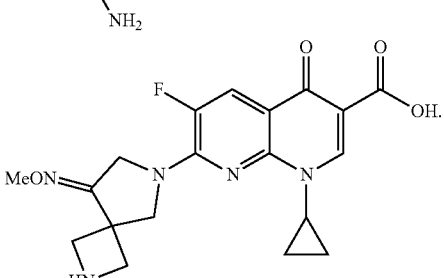

12. A process for the preparation of a compound of Formula IV, comprising the steps of:
preparing a compound of Formula I according to the process of claim 1
oxidizing the compound of Formula I to generate a compound of Formula II; and
reacting the compound of Formula II under a suitable condition to generate the compound of Formula IV,

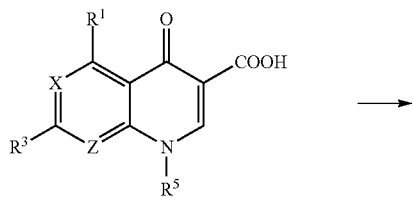

Formula II

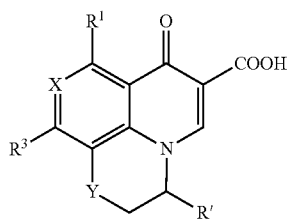

Formula IV wherein in Formula II, Z is $CR^4$, $R^4$ is halo or amino, and $R^5$ is alkyl substituted with OH or SH;
wherein in Formula IV, X, $R^1$, $R^2$ and $R^3$ are as defined in Formula II, Y is O or S, and R' is alkyl;
wherein:
optionally, $R^5$ is $C_{1-6}$ alkyl substituted with OH or SH; or
optionally, $R^5$ is $C_{1-4}$ alkyl substituted with OH or SH; or
optionally, $R^5$ is ethyl or isopropyl each substituted with OH or SH; or optionally, the compound of Formula IV is selected from the group consisting of:

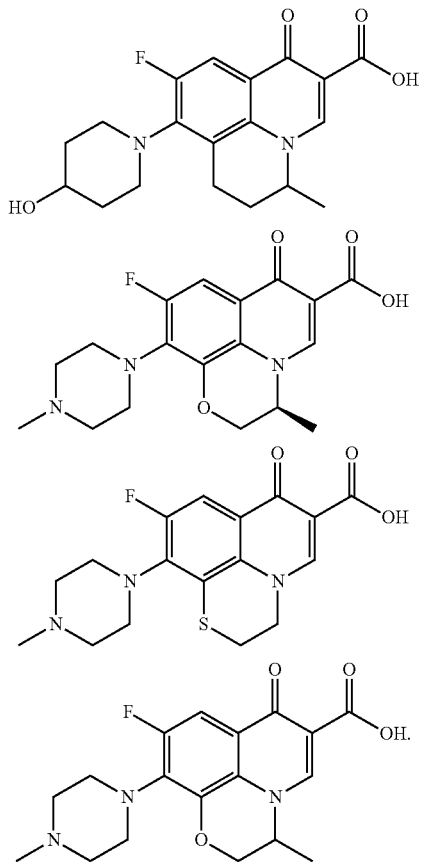

* * * * *